United States Patent
Vendrell

(10) Patent No.: US 10,102,348 B2
(45) Date of Patent: Oct. 16, 2018

(54) IMAGE BASED MEDICAL REFERENCE SYSTEMS AND PROCESSES

(71) Applicant: Ikonopedia, Inc., Dallas, TX (US)

(72) Inventor: Michael J. Vendrell, Dallas, TX (US)

(73) Assignee: Ikonopedia, Inc

( * ) Notice: Subject to any disclaimer, the term of this patent is extended or adjusted under 35 U.S.C. 154(b) by 207 days.

(21) Appl. No.: 13/907,304

(22) Filed: May 31, 2013

(65) Prior Publication Data
US 2013/0326386 A1 Dec. 5, 2013

Related U.S. Application Data

(60) Provisional application No. 61/654,007, filed on May 31, 2012, provisional application No. 61/666,492, filed on Jun. 29, 2012, provisional application No. 61/674,773, filed on Jul. 23, 2012.

(51) Int. Cl.
| | |
|---|---|
| *G06F 3/048* | (2013.01) |
| *G06F 19/00* | (2018.01) |
| *G16H 30/00* | (2018.01) |
| *G16H 50/70* | (2018.01) |
| *G16H 50/30* | (2018.01) |
| *G16H 15/00* | (2018.01) |

(52) U.S. Cl.
CPC ........ *G06F 19/3487* (2013.01); *G06F 19/321* (2013.01); *G16H 15/00* (2018.01); *G16H 30/00* (2018.01); *G16H 50/30* (2018.01); *G16H 50/70* (2018.01)

(58) Field of Classification Search
CPC ............... G06Q 50/24; G06F 19/3487; G06F 19/32–19/324; G16H 10/0065; G16H 15/00; G16H 70/00–70/60; G16H 80/00
See application file for complete search history.

(56) References Cited

U.S. PATENT DOCUMENTS

| | | | |
|---|---|---|---|
| 4,710,876 A | 12/1987 | Cline et al. | |
| 4,729,098 A | 3/1988 | Cline et al. | |
| 5,325,293 A * | 6/1994 | Dorne | G06F 19/328 705/2 |
| 5,625,354 A | 4/1997 | Lerman | |
| 5,987,345 A | 11/1999 | Engelmann et al. | |
| 5,987,459 A | 11/1999 | Swanson et al. | |
| 6,381,710 B1 * | 4/2002 | Kim | 714/45 |

(Continued)

OTHER PUBLICATIONS

PenRad: Read. Report. Track. Manage; Breast Density Assessment Tools; [online]; 3 pp. Retrieved from the internet on May 29, 2013: http://www.penrad.com/products_penrad-MIS_16.html; n.d.

(Continued)

*Primary Examiner* — Kevin L Young
*Assistant Examiner* — Linda Huynh
(74) *Attorney, Agent, or Firm* — Ferguson Braswell Fraser Kubasta PC; Elizabeth Philip Dahm; Kelly J. Kubasta

(57) ABSTRACT

An image-based diagnostic system may include graphical user interfaces that include image icons. Users may select image icon(s) and/or other icon(s) related to an analysis of expert images, such as medical images. Analytical reports may be generated based on the selection(s). In some implementations, the image icons may be correlated to reference information and references may be retrieved based on image icon(s).

22 Claims, 21 Drawing Sheets

(56) References Cited

U.S. PATENT DOCUMENTS

| | | | |
|---|---|---|---|
| 6,785,410 | B2 | 8/2004 | Vining et al. |
| 7,058,650 | B2 | 6/2006 | Yang et al. |
| 7,289,651 | B2 | 10/2007 | Vining et al. |
| 7,792,778 | B2 † | 9/2010 | Zhou |
| 7,979,383 | B2 † | 7/2011 | Heilbrunn |
| 8,369,585 | B2 † | 2/2013 | Graessner |
| 2003/0212576 | A1* | 11/2003 | Kim .................. G06F 19/328 705/2 |
| 2004/0068170 | A1* | 4/2004 | Wang et al. .................. 600/407 |
| 2004/0247166 | A1* | 12/2004 | Giger .................. G06F 19/321 382/128 |
| 2005/0075544 | A1* | 4/2005 | Shapiro et al. .................. 600/300 |
| 2005/0107690 | A1 | 5/2005 | Soejima |
| 2005/0192844 | A1* | 9/2005 | Esler .................. G06Q 10/10 705/3 |
| 2006/0236265 | A1* | 10/2006 | Bowers .................. G06F 9/453 715/809 |
| 2006/0274928 | A1* | 12/2006 | Collins .................. A61B 6/00 382/132 |
| 2006/0277073 | A1* | 12/2006 | Heilbrunn .................. G16H 15/00 705/3 |
| 2007/0041623 | A1* | 2/2007 | Roehrig et al. .................. 382/128 |
| 2007/0122021 | A1* | 5/2007 | Zingaretti et al. .................. 382/132 |
| 2007/0197909 | A1* | 8/2007 | Kariathungal et al. .................. 600/437 |
| 2007/0280525 | A1* | 12/2007 | Basilico et al. .................. 382/132 |
| 2008/0069416 | A1* | 3/2008 | Luo .................. 382/128 |
| 2008/0155451 | A1* | 6/2008 | Lundstrom et al. .................. 715/772 |
| 2008/0155468 | A1* | 6/2008 | Rosander et al. .................. 715/810 |
| 2008/0159613 | A1* | 7/2008 | Luo et al. .................. 382/131 |
| 2008/0208781 | A1* | 8/2008 | Snyder .................. 706/20 |
| 2008/0228686 | A1* | 9/2008 | Fischer et al. .................. 706/46 |
| 2008/0267473 | A1* | 10/2008 | Wang et al. .................. 382/130 |
| 2008/0301571 | A1 | 12/2008 | Herzog |
| 2009/0074273 | A1* | 3/2009 | Fischer et al. .................. 382/128 |
| 2009/0185732 | A1* | 7/2009 | Zhang et al. .................. 382/132 |
| 2009/0228792 | A1* | 9/2009 | van Os et al. .................. 715/702 |
| 2009/0232376 | A1* | 9/2009 | Raundahl et al. .................. 382/131 |
| 2009/0271738 | A1* | 10/2009 | Glaser-Seidnitzer .................. G06F 3/0482 715/821 |
| 2009/0296882 | A1 | 12/2009 | Gkanatsios et al. |
| 2010/0063842 | A1* | 3/2010 | Carroll et al. .................. 705/3 |
| 2010/0125175 | A1* | 5/2010 | Vallone .................. 600/300 |
| 2010/0135562 | A1 † | 6/2010 | Greenberg |
| 2010/0145720 | A1* | 6/2010 | Reiner .................. G06Q 50/205 705/2 |
| 2010/0189313 | A1 † | 7/2010 | Prokoski |
| 2010/0246884 | A1* | 9/2010 | Chen et al. .................. 382/103 |
| 2010/0293164 | A1 † | 11/2010 | Weese |
| 2011/0026791 | A1* | 2/2011 | Collins et al. .................. 382/131 |
| 2011/0028825 | A1 | 2/2011 | Douglas et al. |
| 2011/0110576 | A1* | 5/2011 | Kreeger .................. G16H 50/50 382/132 |
| 2011/0125526 | A1* | 5/2011 | Gustafson .................. 705/3 |
| 2011/0137132 | A1* | 6/2011 | Gustafson .................. 600/300 |
| 2011/0286647 | A1 | 9/2011 | Cao et al. |
| 2011/0255760 | A1 † | 10/2011 | Mahesh |
| 2011/0268336 | A1* | 11/2011 | Dmitrieva et al. .................. 382/131 |
| 2011/0295790 | A1 † | 12/2011 | Zillner |
| 2012/0004932 | A1 | 1/2012 | Sorkey et al. |
| 2012/0020536 | A1 † | 1/2012 | Moehrle |
| 2012/0114213 | A1* | 5/2012 | Buelow et al. .................. 382/131 |
| 2012/0147010 | A1* | 6/2012 | Schmidt et al. .................. 345/440 |
| 2012/0189176 | A1* | 7/2012 | Giger .................. G06K 9/6253 382/128 |
| 2012/0290957 | A1* | 11/2012 | Chernilo .................. G06F 19/3406 715/764 |
| 2013/0006654 | A1 | 1/2013 | Hermans |
| 2013/0055161 | A1* | 2/2013 | Adams .................. G06F 17/30994 715/811 |
| 2014/0149407 | A1* | 5/2014 | Qian et al. .................. 707/737 |

OTHER PUBLICATIONS

PCT International Search Report and Written Opinion dated Jan. 7, 2014 for corresponding PCT Application No. PCT/US/2013/043784 (10 pages).

PenRad; Read. Report. Track. Manage; Breast Density Assessment Tools; [online]; 3 pp. Retrieved from the Internet on May 29, 2013: http://www.penrad.com/products_penrad-MIS_16.html; n.d.

\* cited by examiner
† cited by third party

805 FIG. 9E
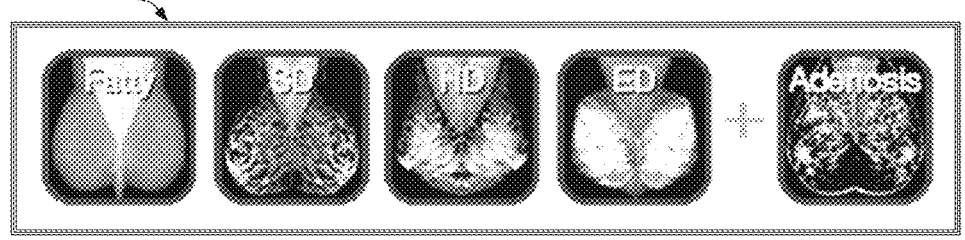
1500 FIG. 15
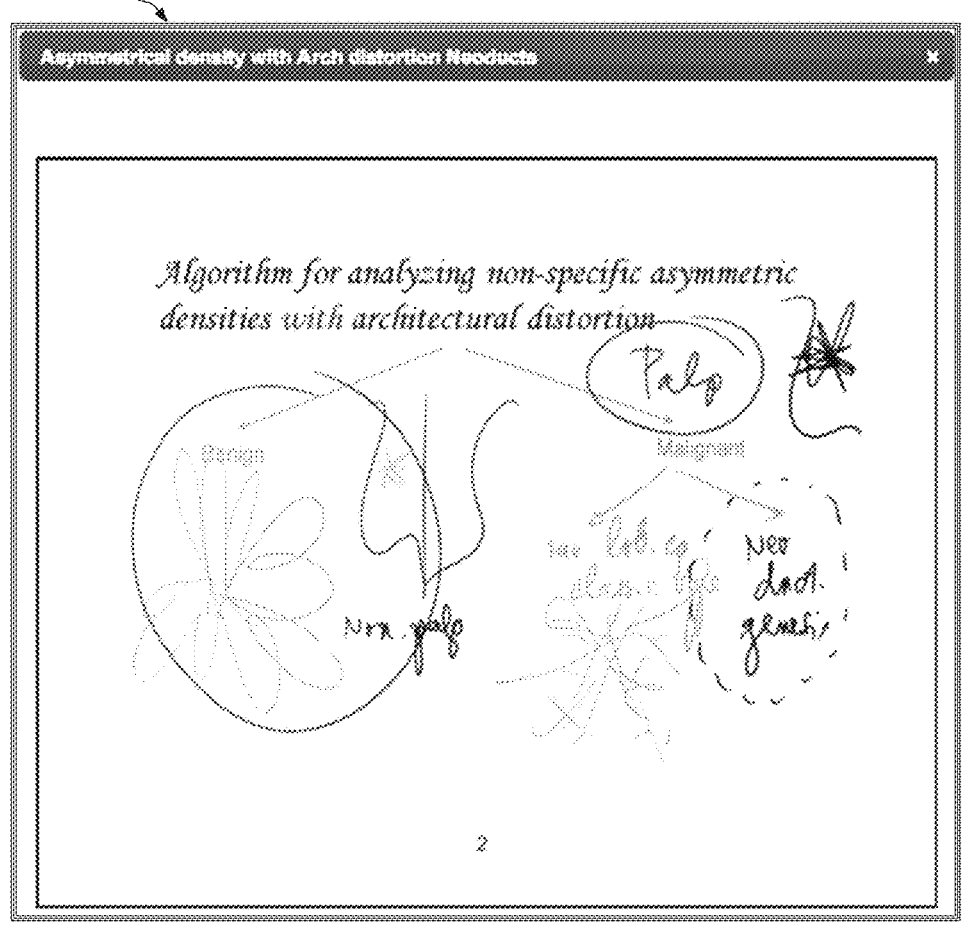

FIG. 12

IMAGE BASED MEDICAL REFERENCE SYSTEMS AND PROCESSES

CROSS-REFERENCE TO RELATED APPLICATIONS

This application claims priority to U.S. Provisional Patent Application No. 61/654,007, entitled "SYSTEM AND METHOD FOR IMAGE-BASED INDEXING, REPORTING AND ANALYSIS OF RADIOLOGICAL DATA", filed on May 31, 2012; U.S. Provisional Patent Application No. 61/666,492, entitled "IMAGE BASED DIAGNOSTIC SYSTEM", filed on Jun. 29, 2012; and U.S. Provisional Patent Application No. 61/674,773, entitled "IMAGE BASED DIAGNOSTIC SYSTEM", filed on Jul. 23, 2012, all of which are hereby incorporated by reference for all purposes.

COPYRIGHT RIGHTS

A portion of the disclosure of this patent document contains material, which is subject to copyright protection. The copyright owner has no objection to the facsimile reproduction by any one of the patent document or the patent disclosure, as it appears in the Patent and Trademark Office patent file or records, but otherwise reserves all copyright rights whatsoever.

TECHNICAL FIELD

The present invention relates to an image based system that allows retrieval of references.

BACKGROUND

With the introduction of electronic records (e.g., electronic medical records and/or other types of files) and digitized test results, a user, such as a physician can often form a diagnosis or other type of analysis while viewing appropriate records on a computer monitor.

SUMMARY

An image-based analysis may facilitate the formation of an analysis and/or entry of an analysis by a user. An analytic graphical user interface (GUI) may include image icon(s), which may include a photographic image.

For example, in some implementations the analytic graphical user interface may be utilized in a medical environment. The image based diagnostic system (e.g., analytic graphical user interface) may facilitate the process of forming a diagnosis through the use of an image based graphical user interface. A user, such as a physician, may view electronic and/or digitized test results through commercially available software. The image based diagnostic system may streamline the process of recording diagnoses through a graphical user interface that includes image icons. The selection of image icons may automatically generate reports and related data may be tracked, as appropriate.

In some implementations, a user may utilize the image based graphical user interface to research topics. A user may select an image icon and references related to the image icon may be retrieved and presented to the user. Allowing a user to search through a plurality of references by selecting an image may allow the user to further research topics while lacking knowledge of the appropriate search term and/or more quickly research topics by reducing the time spent formulating appropriate keywords for queries.

In various implementations, a graphical user interface, for presentation on a user device, may be generated. The graphical user interface may include a plurality of image icons, and each image icon may include at least a portion of a medical photographic image of an example characteristic. A selection of one or more of the image icons and a request for reference information associated with at least one of the selected image icons may be received. A first set of reference information may be retrieved from a memory, such as a database, based at least partially on at least one of the selected image icons. The reference information in the memory may be indexed based at least partially on one or more relationships to one or more of the image icons.

Implementations may include one or more of the following features. At least a portion of the retrieved reference information may be presented on the user device. In some implementations, a second set of reference information may be retrieved based on a secondary association. The secondary association may relate reference(s) in the second set of reference information with the first set of reference information and/or one of the selected image icons. At least a portion of the second set of reference information may be presented to a user. At least one of the image icons may include: characteristic image icon(s) that includes at least a portion of a photographic image associated with a medical characteristic; and/or breast density image icon(s) that include at least a portion of a photographic image associated with breast density. The generated graphical user interface may include association icons. A selection of association icon(s) may be received, and the first set of information may be retrieved based at least partially on the selected image icons and at least one of the selected association icons. The graphical user interface generated may be related to patient test result(s) presented to a user via a third party interface. In some implementations, anatomical location(s) may be received via the generated graphical user interface, where a anatomic location indicates at least a portion of a patient presented in at least one of the patient test results; a selection of image icon(s) to associate with at least one of the received anatomical locations may be received related to a diagnosis based at least partially on the presented patient test results; and, a report may be automatically generated that includes at least a portion of a diagnosis for a patient based on at least one of the selected image icons. Follow-up information may be received for one or more patients and compared with image icon(s) previously selected for each of the patients. Errors based on a comparison of the follow up information and the image icons previously selected may be determined, and a third set of reference information may be identified based at least partially on the determined errors and/or the previously selected image icons associated with the determined errors. In some implementations, an error notification to a user based on the determined errors, wherein the error notification comprises a listing of the identified third set of reference information.

In various implementations, a graphical user interface may be generated that includes a plurality of image icons for presentation to a user. Each image icon may include at least a portion of a medical photographic image of an example of a characteristic. A selection of image icon(s) and a request for reference information associated with at least one of the selected image icon(s) may be received. A first set of reference information may be retrieved from a memory, such as a database, based at least partially on the selected image icons. Reference information in the database may be indexed based on relation to an image icon in the plurality of image icons.

Implementations may include one or more of the following features. At least a portion of the retrieved reference information may be presented on the user device. Image icons may include: a characteristic image icon that includes at least a portion of a photographic image associated with a medical characteristic; and/or a breast density image icon that includes at least a portion of a photographic image associated with breast density. The graphical user interface may include a plurality of other icons related to one or more diagnoses. A selection of one or more other icons and a request for reference information associated with at least one of the selected other icons may be received. A second set of reference information may be retrieved from a memory, such as a database, based on at least one of the selected other icons. The reference information in the database may be indexed based on relation to an other icon. The generated graphical user interface may include: breast images and/or other icons associated with breast images. The breast images may include a first breast image that includes a representation of a breast and lymph nodes proximate the breast, and a second breast image that includes a transverse view of the breast. A selection of an anatomic location on at least one of the breast images and selection of one or more other icons may be utilized to generate a diagnosis. In some implementations, a selection of at least one other icon and a request for reference information associated with at least one of the selected other icons may be received; and a second set of reference information may be retrieved from a memory, such as a database, based on at least one of the selected other icons. Reference information in the database may be indexed based on relation to an other icon. In some implementations, a listing of the first set of references may be generated and presented to a user. A selection of a reference from the listing may be received, and the selected reference may be retrieved.

In various implementations, an image indexed reference system may include a memory and an image-indexing module. The memory may store reference information and association(s) between reference information and image icon(s) in a graphical user interface that includes a plurality of image icons for presentation to a user. Each image icon may include at least a portion of a medical photographic image of an example of a medical characteristic. The image-indexing module may receive a selection of image icon(s) from the graphical user interface and a request for reference information associated with at least one of the image icons. The image-indexing module may determine a first set of reference information associated with the selected image icon based on at least one of the stored associations, and retrieve at least a portion of the first set of reference information from the memory.

Implementations may include one or more of the following features. The memory may store secondary associations between the reference information and the image icons. The image-indexing module may transmit a notification to the user based on the secondary association and the selected image icons, and retrieve at least a portion of a second set of reference information based at least partially on the secondary associations. The secondary associations may include related characteristics, similar characteristics, and/or misdiagnosed related characteristics. The image-indexing module may present at least a portion of the first set of reference information from the memory. The memory may store one or more variation images. The image-indexing module may receive a request for one or more variation images, and retrieve variation image(s) associated with at least one of the selected image icons. The information may include one or more expert verified references.

The details of one or more implementations are set forth in the accompanying drawings and the description below. Other features, objects, and advantages of the implementations will be apparent from the description and drawings.

BRIEF DESCRIPTION OF THE DRAWINGS

For a more complete understanding of this disclosure and its features, reference is now made to the following description, taken in conjunction with the accompanying drawings, in which:

FIGS. 7A-7D illustrate implementations of example worklist graphical user interfaces.

FIG. 9E illustrates an implementation of a portion of the example diagnosis graphical user interface illustrated in FIG. 9A.

FIG. 12 illustrates an implementation of an example report graphical user interface.

FIG. 15 illustrates an implementation of an example graphical user interface presenting a reference material.

DETAILED DESCRIPTION

Figure 1A:
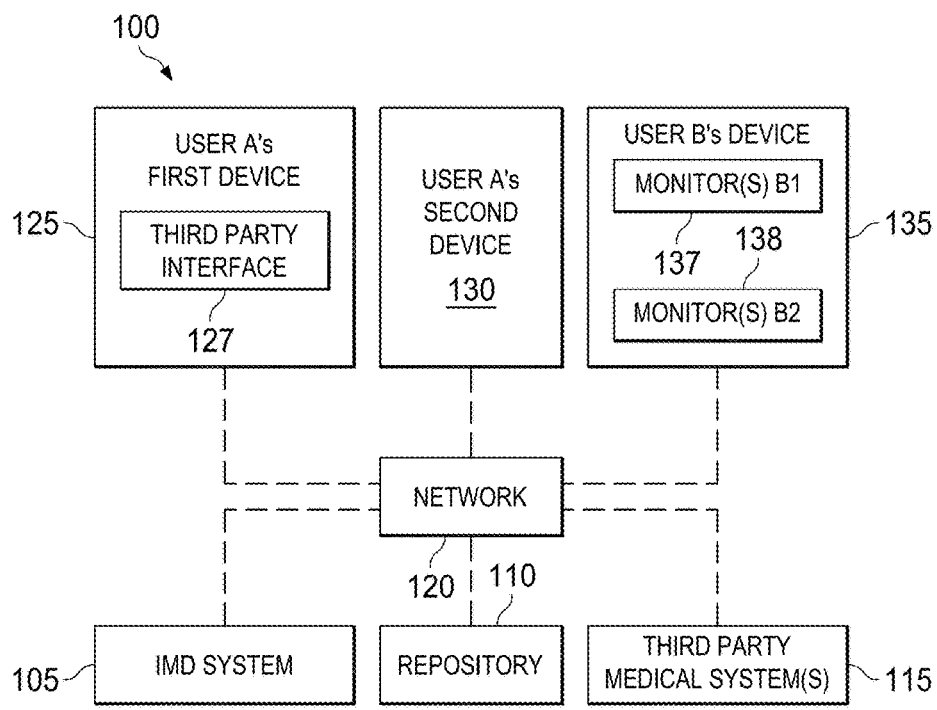
FIG. 1A illustrates an implementation of system that includes an example image based diagnostic system.

Records and/or test results are often electronically presented to users. Providing systems and processes to allow electronic entry and/or formation of the analysis of the test results may improve turnaround time, accuracy, and/or uniformity of analysis reports for aggregation of results. In various implementations, users may utilize an image-based analytic (IMA) system to provide and/or formulate analyses based on test results. The IMA system may include image icon(s) and other icon(s). Selection of the image icon(s) and/or the other icon(s) may allow the IMA system to generate analyses reports. In some implementations, a user may view test results and provide an analysis of the test results via selection of one or more image icons on a graphical user interface (GUI) generated by the IMA system. The IMA system may generate one or more reports based the icon(s) selected by the user. In various implementations, the IMA system may allow image-based research. The IMA system may be used in a variety of environments, such as medical environments, structural analyses, geotechnical analysis, and/or other environments.

In some implementations, a user, in a medical environment, may access an IMA such as an image-based medical diagnostic (IMD) system. A user, such as a physician, may view medical images such as patient test results (e.g., radiographs, ultrasound scans, MRI scans, nuclear medicine scans, and/or computed tomography [CT] scans) and formulate a diagnosis based on the medical images. For example, a radiologist may view and analyze CT scans to determine if a benign mass exists and/or aneurism is present.

An image based medical diagnostic system (IMD system) may generate graphical user interface(s) (GUI) that allow selection of image icon(s) on the GUI(s) to automatically prepare diagnoses of test results, such as patient test results that include one or more medical images. The user may research and/or obtain further information about image icons, and thus diagnoses, through the IMD system. The IMD system may utilize a plurality of image icons in various GUIs.

An image icon is an icon that includes at least a portion of a photographic image. A photographic image may include an image created by a lens or a sensor such as an image created on a photographic film or an electronic image. A photographic image may be 2D or 3D. For example, the photographic image may include medical photographic images such as photographic images obtained from MRI scans, nuclear medicine scans, CT scans, ultrasounds, and/or radiographs. The image icon may be an example, such as a typical presentation, of a diagnosis or portion thereof (e.g., a characteristic of a diagnosis). For example, the image icon may include at least one photographic image of an example of a characteristic. A characteristic may include a property, appearance, and/or other information related to one or more analyses or portions thereof, (e.g., the characteristic may be present in test results). For example, in a medical environment, a characteristic may be a medical characteristic, which describes, provides information related to, and/or differential information related to a diagnosis and/or portions thereof. The image icon may be an image of a particular characteristic of a diagnosis selected by, for example, an expert or other authority in the field. For example, the medical photographic image utilized in the image icon may be selected from a plurality of presentations of a particular characteristic and/or diagnosis from a plurality of patients (e.g., the image in the image icon is not from the test results being analyzed and/or from the other test results associated with the same patient). For example, the image icon may include a photographic medical image from a previously diagnosed presentation of a diagnosis in another patient. In various implementations, the image icons may include text. The text of the image icon may at least partially describe at least a portion of the photographic image in the image icon. For example, an image icon may include a portion of a CT scan of showing a calcification and the image icon may include text, such as "calcification". The text may overlap at least a portion of the photographic image on the image icon.

In some implementations, utilizing image icons that include photographic images, as opposed to representations and/or drawings, may facilitate use of the IMD system by a user, increase accuracy, and/or increase efficiency (e.g., by reducing time spend per selection of an image icon). For example, the user may not need to translate what a representation and/or drawing is illustrating, but rather the user may quickly view the photographic image in the image icon that may present similarly to a presentation of a characteristic in a patient test result. In some implementations, accuracy may be increased by using photographic images in image icons since obvious errors (e.g., misstrike a key and/or inadvertent selections) may be quickly apparent to a user since the photographic image of the image icon should represent the same characteristic as the user is identifying on the patient test results.

Utilizing an IMD system may allow a user, such as a radiologist or pathologist, who analyzes medical images (e.g., electronic and/or non-electronic medical images) to continue to use the right side of the brain, associated with studying images, to generate diagnoses reports related to viewed medical images (e.g., patient test results). Free-form and/or structured language reporting may be viewed as left-brain activity. Continued repetitive switching between right-brain and left-brain activity, as often occurs when physicians view images and then enter/dictate language based reports, may prematurely fatigue a user. Utilizing a graphical user interface with image icons may reduce fatigue associated with switching between right-brain and left-brain activity by allowing a user to utilize right-brain activity while selecting image icons.

In various implementations, determining a diagnosis through image icons generated in a GUI of the IMD system may increase the speed and accuracy of diagnoses provided by users. For example, a user examining a CT scan may be able to quickly identify a lesion from the image disposed on and/or that is a portion of the image icon. In some implementations, if a user suspects a first diagnosis and then selects the image icon associated with the first diagnosis, if the first diagnosis is incorrect, the user may notice that the presentation shown in the image icon is different than the presentation shown in the patient' test result. Thus, the user may notice that the first diagnosis is incorrect and re-analyze the patients test results, search for variations in presentation, request reference materials, ask a colleague for assistance, etc.

Utilizing an IMD system may allow a user to generate diagnostic reports using predetermined common terminology with other users. The use of common terminology may facilitate searching reports; aggregation of reports or outcomes; and/or conducting literature reviews of diagnoses. Common terminology use may be based, in some implementations, on government regulations, business practices, and/or industry preference.

In some implementations, greater efficiency may be found through the automatic and contemporaneous (e.g., contemporaneous with the viewing of medical images and/or with the formation of the diagnosis) generation of the diagnostic report. For example, a user may review and/or edit the report while the analyses of medical images is fresh in the user's mind. Errors due to transcription and/or voice recognition, which may be often found in dictated diagnoses reports, may be reduced and/or may be more likely to be caught (e.g., since the patient's case history is fresh in the user's mind) since the system automatically generates reports contemporaneously based on image icon selection by a user.

FIG. 1A illustrates a system 100 that may be utilized to provide access to the IMD system (e.g., a computer system, such as a web server). One or more users, such as user A and user B, may access the IMD system 105, a Repository 110, and/or Third Party Medical System(s) 115 through a network 120 (e.g., Internet and/or LAN). For example, medical images (e.g., patient test results) for viewing and/or analysis by a user may be viewed utilizing commercially available software (e.g., commercially available medical image viewing software, such as RIS/BRIS modules available from GE, Phillips, Siemens, McKesson; Hologic and may include MRI, CT scan, PET scan, ultrasound, and/or radiographs). The medical images may be stored in the repository 110 coupled to the user device(s) 125, 130, 135 and/or the third party medical system 115. The commercially available software may also include patient information, such as patient history and/or previous tests and/or results. (e.g., via an electronic medical record and/or appropriate commercially available viewing software). The image based diagnostic system 105 may communicate (e.g., through one or more application interfaces) with the medical image viewing software, such third party medical systems 115, to retrieve and/or display patient history and/or previous tests and/or results. The image based diagnostic system may confirm diagnosis information is being associated with the appropriate patient by communicating with the medical image viewing software. For example, when a user selects a patient for which to provide a diagnosis, the IMD system 105 may communicate with the third party system 115 to determine whether the selected patient is the same as the patient associated with the test results being presented by the third party system.

The users may each utilize one or more user devices (e.g., computer such as laptops, desktops, specialized computers, tablet computers, and/or smart phones) to access various parts of the system 100. As illustrated, user A may utilize a first device 125 and a second device 130, and user B may utilize a user device 135 that includes more than one monitor, such as Monitors B1 137 and Monitors 138.

Figure 1B:
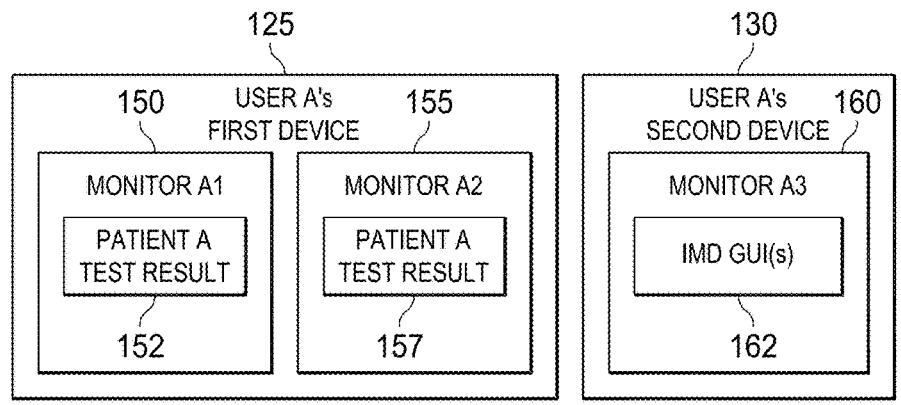
FIG. 1B illustrates an implementation of a portion of an example user device, illustrated in FIG. 1A.

User(s) may access various parts of the system 100 through various user devices or portions thereof. For example, user A may access medical images, such as patient test results (e.g., CT scan(s), MRI scan(s), ultrasounds, and/or radiograph(s)), which are viewable through a third party medical system 115, via a third party interface 127, a portion of which resides on User A's first device 125. As illustrated in FIG. 1B, patient A test results 152 are presented on monitor A1 150 and patient A test results 157, which may be different from test results 152, are presented on monitor A2 155 of User A's first device 125. User A may access the IMD system 105 and/or view GUIs generated by the IMD system through the User A's second device 130. As illustrated in FIG. 1B, the IMD GUI(s) 162 may be presented on monitor A3 160 of User A's second device 130.

As illustrated in FIG. 1A, some users, such as user B, may access various parts of the system through the same user device, such as user B device 135. For example, patient test results may be presented on Monitor(s) B1 137 and IMD GUIs may be presented on Monitors B2 138 of user B's device 135.

For example, the described system may be utilized in a radiology reading room where one or more radiologist access third party systems to view medical images, such as patient test results stored on a repository coupled to the system, and access the IMD system through which diagnoses of patient test results are provided.

FIG. 1A illustrates an implementation of an example image-based medical diagnostic (IMD) system 105. The IMD system 105 may include a server, such as a web server. The IMD server 105 may include a processor that executes instructions and manipulates data to perform operations of server and a memory. The memory may include a repository of data. Data may include various image icons, various text icons, coding (e.g., diagnostic coding, medical billing coding), data related to medical diagnoses, uniform/common terminology for diagnoses, user metrics, practice metrics, diagnosis outcome metrics, monitoring information related to government and/or industry standards, tracking information related to medical diagnoses, tracking information related to users, variations in presentations, reference materials, and/or other information. Data may include image-indexed reference materials. The image-indexed reference materials may include medical references (e.g., videos, journal articles, diagnostic references and/or images) that are correlated to and/or approximately related to image icons of the IMD system. The medical references may be expert reviewed and/or selected. Selection of an image icon may retrieve correlated data and/or references. For example, references and/or image icons may be associated by one or more associations (e.g., primarily related and/or secondarily related, such as presentations often confused for each other, similar presentations, etc.) Text based searching and/or indexes may also provide a process for searching the information in the image-indexed reference. The data and/or portions thereof may be alternatively and/or additionally stored in a repository coupled to the server.

The memory of the IMD system 105 may store various modules (e.g., diagnosis module(s), reference module(s), monitoring module(s), and/or communication module(s)). For example, interfaces, such diagnosis interfaces for receiving, presenting and/or generating medical diagnoses and/or reference interfaces for accessing image-indexed references may be generated by one or more of the modules stored in the memory. The module(s) stored in a memory of the IMD system 105 may perform one or more of the described processes. The graphical interfaces may facilitate interaction between a user and the diagnostic interface and/or reference interface. The modules may also generate communication interface coupled to the other interfaces (e.g., an interface to communicate with commercially available software for medical image viewing and/or electronic medical record software). The communication interface may access data upon request from other interfaces (e.g., diagnostic modules) and/or access to various forms of data. Memory may include any appropriate type of memory.

A communication interface of the IMD system 105 may allow the server of the IMD system to communicate with other repositories and/or user devices via the network 120. The communication interface of the IMD system 105 may transmit data from server and/or received data from coupled repositories and/or other user devices via network protocols (e.g., TCP/IP, Bluetooth, and/or Wi-Fi) and/or a bus (e.g., serial, parallel, USB, and/or FireWire).

Data useful to the system may be stored in repositories in a location or a plurality of locations, such as in a memory of the IMD system 105 and/or remote to the server in one or more repositories 110. For example, data, such as patient test result(s) and/or patient information may be stored in one or more of the additional repositories 110. Additional repositories 110 may be coupled to the IMD system 105 via a network 120. Diagnosis and/or reference interface may utilize the communication interface of the IMD system 105 to access data on the additional repositories 110. Remote, as used herein, means any component, object, value, variable, and/or data and/or data schema that is not directly processable, accessible, or otherwise capable of communicating with server. Indeed, remote data is merely in terms of IMD server—in other words, the remote data is typically remote to IMD server but may be local to server or even physically resident on a client (e.g., user device) coupled to the server.

The user devices 125, 130, 135 may be clients of the IMD system 105. For example, clients, such as user A first device 125, user A second device 130, and/or user B device 135, may allow a user, such as a radiologist, to access a server and/or interfaces stored on a memory of the IMD system 105. In some implementations, interface(s) of the IMD system 105 and/or portions thereof may be stored on a user device 125, 130, 135. Portions of the interface(s) stored on the user device 125, 130, 135 may be updated and/or altered by updates pushed from the IMD server (e.g., the IMD server may transmit an update to the user device). A user device 125, 130, 135 may be a computer server such as a personal computer, a laptop, a personal digital assistant, a smart phone, tablet or any computer system appropriate for communicating with the IMD system. In some implementations, user(s) may utilize more than one type of user device (e.g., a desktop and a tablet computer). The user device(s) may include a processor, a memory, a communication interface, and a presentation interface. The processor of a user device may include a programmable logic device, a microprocessor, or any other appropriate device for manipulating information in a logical manner and memory may include any appropriate form(s) of volatile and/or nonvolatile memory, such as a repository. The communication interface of a user device may allow the user device(s) to communication to other computers and/or repositories via a network. The communication interface of a user device may communicate with the IMD server via one or more network protocols (e.g., TCP/IP, Wi-Fi, 802.11g, 802.11n, IR or Bluetooth). A presentation interface of a user device may present data on the client to a user, such as via a monitor and speakers.

One or more graphical user interface (GUI) of the interface(s) generated by the IMD system may be displayed on a presentation interface of the user device, such as a monitor or screen, of the client. GUI may be operable to allow the user of a user device to interact with repositories and/or various interface(s). Generally, GUI provides a user with an efficient and user-friendly presentation of data provided by the IMD system. GUI includes a plurality of displays having interactive fields, such as image icons, text icons, tabs, pull-down lists, fillable fields, and editable text operated by the user. And in one example, GUI presents an explore-type interface and receives commands from the user. It should be understood that the term graphical user interface may be used in the singular or in the plural to describe one or more graphical user interfaces in each of the displays of a particular graphical user interface. Further, GUI contemplates any graphical user interface, such as a generic web browser, that processes information in the IMD system and/or user device and efficiently presents the information to the user. In some implementations, GUI may present a web page embedding content. The server can accept data from a user device(s) via the web browser (e.g., Microsoft Internet Explorer, Safari, or Google Chrome) and return the appropriate Hyper Text Markup Language (HTML) or eXtensible Markup Language (XML) responses.

Although FIG. 1A provides one example of an IMD server that may be used with the disclosure, the server can be implemented using computers other than servers, as well as a server pool. For example, a server may include a general-purpose personal computer (PC), a Macintosh, a workstation, a UNIX-based computer, a server computer, or any other suitable device. According to one implementation, a server may include a web server. Server may be adapted to execute any operating system including UNIX, Linux, Windows, or any other suitable operating system. In short, server may include software and/or hardware in any combination suitable to provide access to data and/or translate data to an appropriate compatible format.

Although a single processor has been described in the IMD server and/or user devices, multiple processors may be used according to particular needs, and reference to processor is meant to include multiple processors where appropriate. Processor may include a programmable logic device, a microprocessor, or any other appropriate device for manipulating information in a logical manner.

A memory of the server, memory of user device(s), and/or additional repositories may be any appropriate form of memory. For example, additional repositories may include a relational database. However, a variety of repositories may be used, such as, SQL databases, relational databases, object oriented databases, distributed databases, XML databases, and/or web server repositories. Furthermore, memory may include one or more forms of memory such as volatile memory (e.g., RAM) or nonvolatile memory, such as read-only memory (ROM), optical memory (e.g., CD, DVD, or LD), magnetic memory (e.g., hard disk drives, floppy disk drives), NAND flash memory, NOR flash memory, electrically-erasable, programmable read-only memory (EEPROM), Ferroelectric random-access memory (FeRAM), magnetoresistive random-access memory (MRAM), non-volatile random-access memory (NVRAM), non-volatile static random-access memory (nvSRAM), and/or phase-change memory (PRAM).

Although FIGS. 1A and 1B illustrate an implementation that may be utilized with the IMD system, other appropriate systems may be utilized. For example, a user may utilize a desktop computer to access third party medical systems, to view patient test results stored in a coupled repository, and/or other medical systems (e.g., hospital and/or clinic systems) and a tablet computer through which diagnoses reports are generated through the IMD system. In some implementations, a user may utilize a laptop computer coupled to monitor(s). The user may utilize a desktop computer and a smart phone, in some implementations.

Although FIGS. 1A and 1B illustrate implementations utilized with the IMD system, similar systems may be utilized with IMA systems, as appropriate. For example, a user may view test results on a first user device via a third party interface. The user may access the IMA system via a network, such as the internet and provide analyses of test results via GUIs generated by the IMA system. In addition, one or more modules of the IMA system may perform various functions similar to the modules of the IMD system and/or one or more memories may store similar data to the IMD system, as appropriate.

Figure 2A:
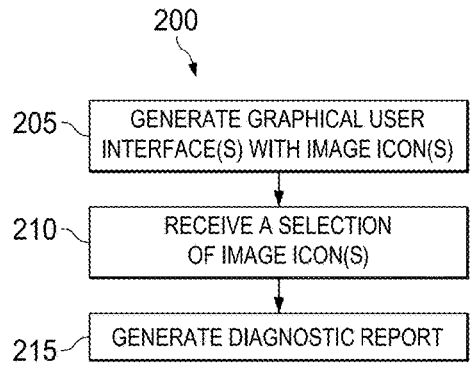
FIG. 2A illustrates an implementation of an example process performed by the IMD system.

FIG. 2A illustrates an implementation of a process 200 performed by the IMD system, such as IMD system 105 illustrated in FIG. 1A, to generate diagnostic report(s). One or more GUI(s) with one or more image icons may be generated (operation 205). For example, a diagnosis module stored in a memory of the IMD system may generate the GUI(s). The GUI(s) may be generated such that one or more diagnoses may be provided by a user through the generated GUI(s). The GUI(s) may include image icons and/or text icons. The image icons may include photographic images. For example, the photographic images may be an example of a characteristic (e.g., a medical characteristic such as breast density, mass, and/or cyst). In some implementations, the photographic images selected to be included in an image icon may include images of lesion characteristics (e.g., calcification, powdery, skin, crushed, lymph node, obscured, and/or lobulated), and/or breast density. The photographic image(s) or portions thereof selected for inclusion in an image icon may be a specific presentation of a characteristic, such as a typical presentation of a characteristic, a presentation of a characteristic most commonly associated with a characteristic, etc. (e.g., as opposed to generating a graphical user interface with image icons that include images selected from the patient test results being analyzed).

A selection of one or more image icons may be received (operation 210). A user may select one or more image icons on the generated GUI(s) through a user device. For example, the user may touch an image icon on a touchscreen of a user device to select the image icon and/or use a pointing device (e.g., mouse, stylus, and/or touchpad) to select the image icon. The user device may transmit the selections of image icons to the IMD system (e.g., through a website generated by the IMD system). The IMD system may receive the selections and/or store the selections.

A diagnostic report may be generated (operation 215). The IMD system may generate the wording of the report diagnosis based on the image icons and/or text icons selected. For example, the a template of possible wording associated with one or more image icons, text icons, and/or combinations thereof may be stored in a memory coupled to the IMD system. The IMD system may determine the wording for a diagnostic report by determining the wording associated with the selected image and/or text icon(s) in the template and generating the diagnostic report based on the determined wording. The diagnostic report may automatically retrieve and/or include patient information, patient test result types being analyzed by the user, and/or one or more generated diagnoses. The diagnostic report may include other information provided by the use, such as follow-up tests recommended, comments, change from previous test results, etc. The diagnostic report may be provided through a GUI (e.g., the report GUI(s)) generated by the IMD system for presentation to a user (e.g., on presentation device of a user device).

Process 200 may be implemented by various systems, such as system 100. In addition, various operations may be added, deleted, and/or modified. For example, user credentials (e.g., user name and/or password) may be received (e.g., through a generated GUI) by the IMD system. In some implementations, the GUI may be generated based at least partially on user credentials. For example, a work-list for the user may be generated based at least partially on user credentials; the GUI may be generated based on clinic preferences, such as a specific variation of a lesion characteristic; and/or the GUI may be generated such that user preferences, such as for home page, colors, etc. are presented. In some implementations, the described process and/or operations thereof may be performed by the IMD system and/or IMA system in other environments (e.g., forensic analysis, body imaging, and/or security screening).

Figure 2B:
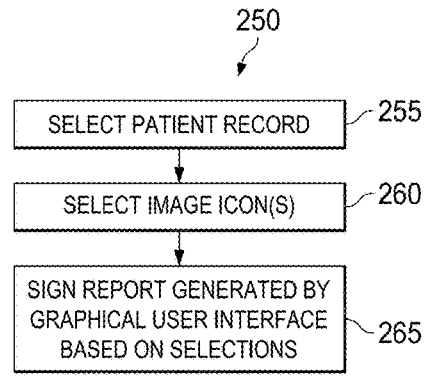
FIG. 2B illustrates an implementation of an example process for generating diagnostic report(s).

FIG. 2B illustrates an implementation of a process 250 for generating diagnostic report(s) through the IMD system. A patient record may be selected (operation 255). For example, the user may login to the IMD system via a website and the GUI generated (e.g., by the IMD system) for presentation to the user may include a work-list that includes a listing of patients which the user must evaluate. In some implementations, the work-list may include a listing of patients associated with test results for analysis by one or more users, and the user may select one or more patients from the listing to provide a diagnosis. The user may select a patient from the worklist through the GUI and the selection may be transmitted to the IMD system.

One or more image icons may be selected (operation 260). The user may view a GUI (e.g., diagnostic GUI) generated by the IMD system that includes image icons and/or text icons. The image icons and/or the text icons may be selected for inclusion in the GUI based at least partially on the type of patient test results (e.g., anatomical location of the imaging in the test result, such as breast imaging; type of machine utilized to provide the test results, such as an MRI; and/or whether the patient test results include previous diagnoses), user properties (e.g., physician specialty, group memberships, and/or compliance requirements), facility properties (e.g., type of clinic and/or hospital), and/or user preferences. The image icons may include at least a portion of a medical photographic image of an example of a medical characteristic. The text icons may include text that describes a portion of a diagnosis and/or information to be included in a diagnosis. For example, text icons may include association icons (e.g., icons that indicate a relationship between two icons such as "and", "or", and/or "versus"), coding icons (e.g., BI-RADS® Category), level of suspicion icons (e.g., benign, mild suspicion, moderate suspicion, arch distortion, high suspicion, and/or malignant mass), notation markers icons (e.g., implant, post-op, marker, negative) and/or comparison icons (e.g., gone, better, same, worse, new when compared with previous test results). The text icons may provide anatomical location information. The user may select one or more of the image icons and/or one or more of the text icons to describe the patient test results. By allowing the user to select image icons, as opposed to dictating and/or typing diagnoses, the user may more quickly and/or accurately provide a diagnosis (e.g., since the user may not have to repeatedly switch between right and left brain activities; since the user may quickly select icons rather than dictating an entire diagnosis; and/or when viewing all the options available for selection on the GUI, the user may be reminded to provide more information such as comparison to previous exam when seeing the icons on the GUI). The selected image icon(s) and/or text icon(s) may be received by the IMD system and/or stored in a memory coupled to the IMD system and/or the user device.

A report generated by the GUI based on the selected image icons may be signed (operation 265). For example, a diagnostic report (e.g., a report including at least a portion of a diagnosis), a billing report (e.g., a report including at least a portion of billing information, such as billing codes and/or insurance provider), compliance report (e.g. a report that includes information to comply with industry, association, and/or government regulations), etc. may be generated.

The report may be stored in a memory coupled to the IMD system. The report may be generated based at least partially on selections of icons, industry criteria, practice group criteria, insurance requirements, governmental requirements, etc. In some implementations, a diagnostic report may be automatically generated by the IMD system based at least partially on selected image icon(s) and/or text icon(s). The diagnostic report may be presented to the user via a GUI of the IMD system. The user may review the diagnostic report and "sign" or otherwise provide approval of the diagnostic report (e.g., select an "approve" button). By allowing the user to contemporaneously view the diagnostic report (e.g., since the diagnostic report is generated by the IMD system, for example, when the user selects a report GUI and/or after receiving a selection of image icon(s)), the user may provide a more accurate and timely diagnostic report. For example, since the patient's case is fresh in the memory of the user, the accuracy of the report may be increased and/or the report may be provided in a more timely manner. In some implementations, unlike when transcription services are provided (e.g., voice recognition and/or human transcription), since the report does not need to be corrected and/or proofread, the amount of time to produce a signed report may be reduced. The signed report may be automatically transmitted, for example, to a referring physician, to a patient, to a hospital, to an insurance company, etc.

Process 250 may be implemented by various systems, such as system 100. In addition, various operations may be added, deleted, and/or modified. For example, after a user logs into the system, the user may be presented a home-screen with a listing of patients whose test results need to be analyzed. The user may select one or more of the patient records to be assigned to his/her caseload. In some implementations, the IMD system may communicate with third party medical systems to determine whether the patient record in which a diagnosis is being provided is the same as the patient record associated with the patient test results being viewed by the user. In some implementations, the described process and/or operations thereof may be performed by the IMD system and/or an IMA system in other environments (e.g., forensic analysis, body imaging, and/or security screening).

Figure 3:
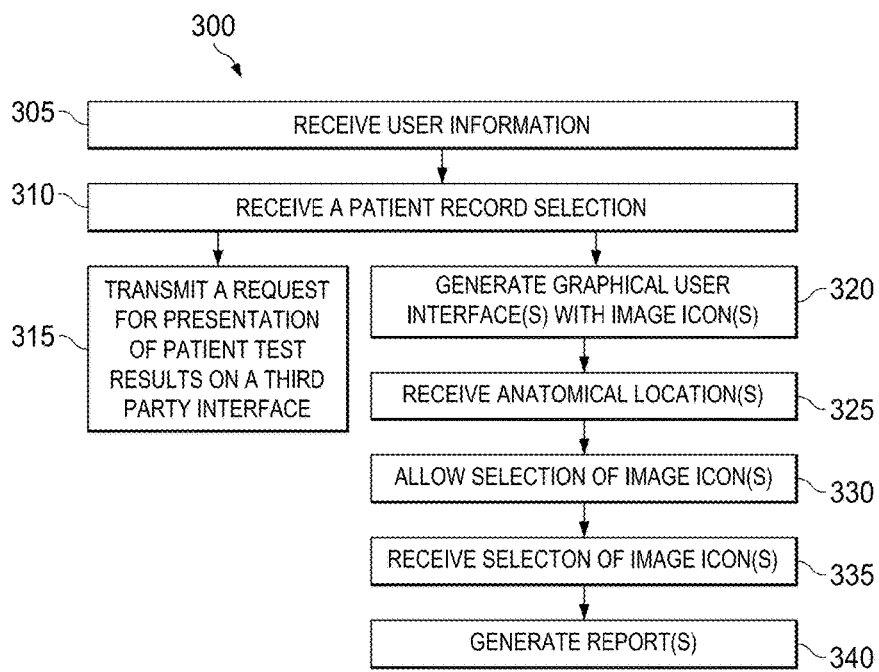
FIG. 3 illustrates an implementation of an example process for receiving diagnosis information.

In some implementations, diagnostic report(s), billing report(s), and/or other report(s) may be generated based on the image icon(s) and/or other icon(s) (e.g., text icons, such as association icons, diagnosis text icons, etc.) selected. FIG. 3 illustrates an implementation of example process 300 for receiving diagnosis information using the IMD system. User information may be received (operation 305). For example, a user may utilize a user device, such as a personal computer, to access an interface of the IMD system (e.g., through the internet) and provide credentials, such as a user name and security information (e.g., password, key code, and/or public key/private key). The IMD system may receive the user information and compare the user information to stored user information (e.g., stored in a memory coupled to the IMD system) to determine whether to allow the user access to at least portions of the IMD system. If a determination is made to allow the user access to the IMD system, then the IMD system may generate GUI(s), such as work-list GUIs, to facilitate the entry of analysis information by the user.

A patient record selection may be received (operation 310). A GUI may be generated by the IMD system to present a listing of patients. For example, a worklist for the user may be generated based at least partially on the received user information. In some implementations, the IMD system may present, via a generated GUI, a listing of patients corresponding to test results to be analyzed for a group of users (e.g., physicians on duty at a hospital, practice group, and/or specialty of a practice group, such as the mammography group of a radiology practice). The user may select a patient record and the selection may be transmitted to the IMD system.

A request for presentation of patient test results on a third party interface may be transmitted to a third party system (operation 315). The IMD system may be coupled directly or indirectly to a third party system, which allows presentation of patient test results on a user device. The IMD system may communicate with the third party system. For example, the IMD system may transmit a request to a third party system, such as a commercially available software platform for viewing patient test results (e.g., medical images, such as CT scans, MRI scans, and/or other medical images), so that test results associated with the received selection of a patient record may be retrieved (e.g., from a repository coupled to the third party system) and presented to the user via the third party system on a user device.

GUI(s) may be generated with one or more image icons (operation 320). For example, a diagnostic GUI may be generated that includes image icon(s) and text icon(s). The image icons may include breast density image icons that include at least a portion of a photographic image associated with an example of a breast density category. For example, a first breast density image icon may include a radiograph of a first breast density category (e.g., defined by industry, government, and/or insurance standards), a second breast density image icon may include a radiograph of a second breast density category, a third breast density image icon may include a radiograph of a third breast density category and fourth breast density image icon may include a radiograph of a fourth breast density image icon. In some implementations, a level of breast density may be required (e.g., by government standards) to be reported to patients and the user may select a level of breast density that corresponds to the breast density depicted in a patient test result through a breast density image icon.

An anatomical location may be received (operation 325). The user may select an anatomical location corresponding to a location on a patient in at least a portion of the patient test results. For example, a right breast, a left breast, or bilateral may be selected as an anatomical location. In some implementations, a specific location on the breast may be indicated using location indicia, such as a circle, dot, highlight, and/or other indicia. In some implementations, a representation of a breast including lymph nodes proximate the breast and/or a transverse view of a breast may be included in the GUI. An anatomical location may be provided by the user by selecting text icons, such as location icons (e.g., relative and/or anatomical location), associated with the breast images. In some implementations, a location icon may be selected via the GUI and transmitted to the IMD system.

Selection of one or more image icons may be allowed (operation 330). When an anatomical location selection is received, selection of image icon(s) may be allowed. For example, selection of image icon(s) may be restricted prior to selecting an anatomical location being selected. In some implementations, the image icon(s) may appear differently when selection is restricted than when the image icon(s) may be selected. For example, the image icon(s) may be have a grey appearance or shading when selection is restricted.

A selection of one or more image icons may be received (operation 335). For example, the user may select breast density image icon. The user may select a characteristic icon that corresponds to at least a portion of a diagnosis. For example, a characteristic icon may be a lesion-characteristic icon, such as an icon indicating calcification or cyst. The characteristic icon, such as the lesion characteristic, may include a photographic image of a visual characteristic. The visual characteristic may be at least partially included in the portion of the photographic image selected for inclusion in the characteristic icon.

Report(s) may be generated (operation 340). For example, reports, such as billing reports, diagnostic reports, compliance reports (e.g., based on metrics and/or required by facilities, such as hospitals, industry requirements, and/or government requirements). In some implementations, a diagnostic report may be generated based on image icon(s) and anatomical location(s) selected. In some implementations, a billing report may be generated based at least partially on the image icon(s), anatomical location(s) and/or diagnostic reports. The billing reports may be generated at least partially based on industry codes, such as CPT and/or ICD-9 codes, and one or more image icons, text icons, and/or combinations thereof may be associated with one or more CPT and/or ICD-9 codes such that billing reports may be generated based on selected icons. In some implementations, one or more compliance reports maybe generated based on user properties (e.g., time spent analyzing patient test results, types of test results analyzed, number of test results analyzed over a time period, and/or other metrics).

Process 300 may be implemented by various systems, such as system 100. In addition, various operations may be added, deleted, and/or modified. For example, one or more report GUI(s) may be generated to present report(s) to the user. In some implementations, the user may transmit notice of approval of the report (e.g., sign a diagnostic report and/or approve automatic transmission of a compliance report to an appropriate entity). In some implementations, the IMD system may determine whether the patient record selected is associated with the test results being presented via a third party system. If the determination is made that the selected patient record is associated with the test results being presented, then selection of one or more image icons and/or anatomical location(s) may be allowed. If the determination is made that the selected patient record is not associated with the test results being presented, then a selection of image icon(s) and/or anatomical location(s) may be restricted; a notification may be transmitted to the user; and/or a message may be transmitted to the third party system (e.g., such that the appropriate test results may be presented to the user). In some implementations, the described process and/or operations thereof may be performed by the IMD system and/or an IMA system in other environments (e.g., forensic analysis, body imaging, and/or security screening).

In some implementations, reference materials may be accessible through IMA systems, such as the IMD system. The reference materials may be accessible independently from the analytical GUIs generated by the IMA system and/or through GUIs that facilitate the receipt of analyses through the IMA system. For example, the image icons presented in a graphical user interface of an IMA system, such as the IMD system, may be correlated to reference information. For example, reference information may be indexed and/or associated with various image icons. The reference information correlated to the image icon may include images and/or text that may be relevant and/or related to the image in the image icon. The reference information may include journal articles, expert opinions, textbooks, videos, variations of presentations and/or other relevant medical reference information. During use, a user may conduct research by selecting an image icon and viewing the correlated reference information. By allowing a user to quickly access information related to a diagnosis and/or potential diagnosis while analyzing patient test results, accuracy may be increased. For example, accuracy may be increased since: research on diagnosis is quickly and easily provided through the interface; since a diagnosis can be researched without knowing key words by using image icons to search references; and/or since variations of presentations of lesions may be quickly searched to provide more accurate diagnoses. In some implementations, users may use the reference materials accessible through the IMA system to retrieve references related to image icon(s) to further study a characteristic in an image icon.

Figure 4:
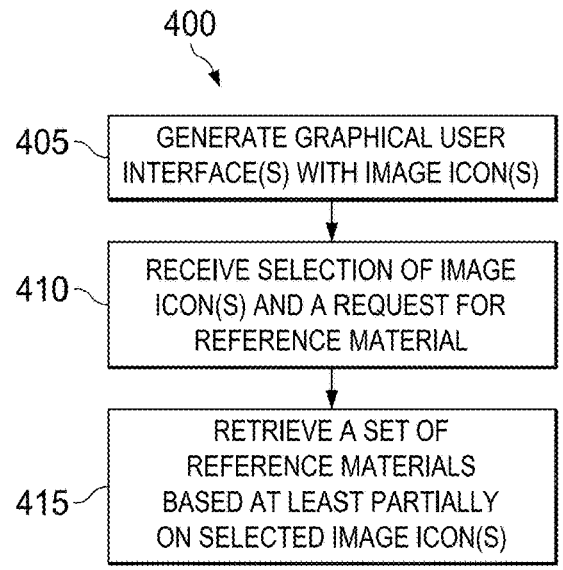
FIG. 4 illustrates an implementation of an example process for retrieving reference materials.

FIG. 4 illustrates an example process 400 for retrieving reference materials. The process 400 may be performed by systems, such as system 100. GUI(s) may be generated including one or more image icons (operation 405). For example, the IMD system may generate interfaces, such as a diagnostic GUI and/or a reference GUI. For example, the diagnostic GUI through which diagnoses may be provided, may be generated with one or more image icons and/or one or more other icons, such as text icons. In some implementations, a reference GUI may be generated that includes image and/or text icons through which reference materials related to the image icons and/or text icons may be retrieved. The GUI may include fields through which the reference materials may be searched. A user may be presented with free-form fields in the diagnosis GUI and/or reference GUI, through which keywords may be provided for a search to be executed upon by the IMD system.

A selection of one or more image icons and a request for reference material may be received (operation 410). For example, a user may double click an image icon on a GUI generated by the IMD system to request reference material associated with the image icon. In some implementations, the user may select an image icon and another icon, such as a reference text icon to request reference material related to the image icon. In some implementations, the user may select more than one image icon and an association icon (e.g., versus) to indicate a relationship among the image icons about which the user would like further information (e.g., reference materials).

A set of reference materials may be retrieved based at least partially on the selected image icon(s) (operation 415). For example, the IMD system may determine a set of reference materials to retrieve based on associations between reference materials, image icon(s), and/or text icon(s) stored in a memory coupled to the IMD system. In some implementations, the set of reference materials may include one or more levels of association, such as a primary association, a secondary association, etc. For example, an image icon may have a primary association with a set of references, such as the set of references primarily associated with the image icon may provide further information about the image icon. An image icon may have a secondary association with a set of references, such as the set of references secondarily associated with the image icon may provide additional information about the image icon (e.g., similar characteristics and/or diagnoses, commonly confused and/or related characteristics and/or diagnoses, etc.).

Process 400 may be implemented by various systems, such as system 100. In addition, various operations may be added, deleted, and/or modified. For example, the set of retrieved materials or a portion thereof (e.g., titles) may be presented to the user. The user may select one or more of the reference materials in the set and the IMD system may present the selected reference material(s) to the user via GUI(s) generated by the IMD system. In some implementations, the GUI with image icons may be generated independently of a patient, test results, and/or patient record. In some implementations, a set of references may be retrieved and recommended to a user and/or group of users (e.g., based on metrics, such as accuracy, error rates, new information, etc.). A user may access image icon-based searching of references while analyzing test results and providing a diagnosis through the IMD system. In some implementations, allowing searching of references based on image icons may be performed independently of providing diagnoses for patients. In some implementations, the described process and/or operations thereof may be performed by the IMD system and/or an IMA system in other environments (e.g., forensic analysis, body imaging, and/or security screening).

In some implementations, various metrics may be monitored, such as user information, user statistics, user group statistics, costs, diagnoses information, error rates, accuracy, outcomes, overall Receiver Operator Characteristic (ROC) curves, ROC curves relative to specific diagnoses, etc. The information may be tracked to comply with government regulations, industry regulations, licensing requirements, and/or to further research and/or educational goals.

Figure 5:
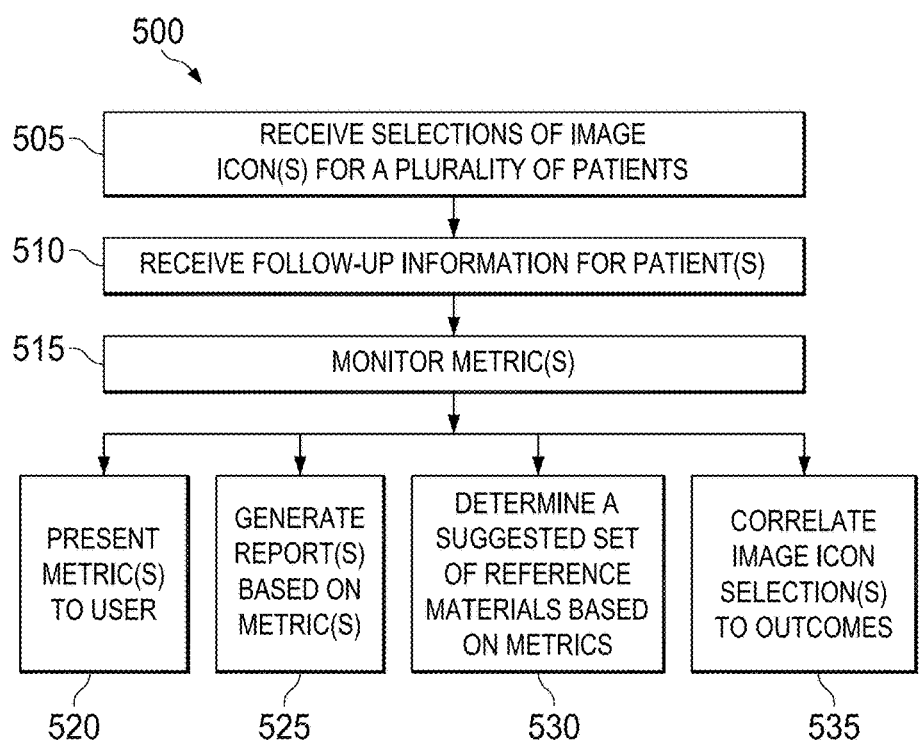
FIG. 5 illustrates an implementation of an example process for monitoring metric(s).

FIG. 5 illustrates an example process 500 for monitoring metric(s). A selection of image icon(s) may be received for a plurality of patients (operation 505). For example, the IMD system may store information provided to the IMD system, such as image icons selected, text icons selected, and/or diagnosis generated, in a memory coupled to the IMD system.

Follow-up information may be received for one or more of the patients (operation 510). Follow-up information may include test results, such as biopsy results, blood tests, etc., related to one or more of the patients. The follow-up information may be transmitted to the IMD system (e.g., automatically and/or by a user) and associated with one or more of the patient records previously stored in a memory coupled to the IMD system.

Metrics may be monitored (operation 515). The data from the stored information, such as selected icon(s) and the follow-up information may be aggregated and/or analyzed to produce one or more metrics (e.g., based on statistical methods and/or commercially available statistical software). Metrics may include: error rates, outcomes associated with diagnoses and/or selected image icons, time spent analyzing images (e.g., per image, per patient, and/or per predetermined category of diagnoses), patient test results analyzed per time period, number of patient records analyzed during a predetermined time period (e.g., per user and/or per groups of users), etc. Metric(s) may be determined based on information provided to the IMD system such as selected icons, follow-up information, time(s), etc. The metrics may be stored in a memory coupled to the system (e.g., user system and/or IMD system) and monitored. One or more statistical analyses may be performed to the stored metrics to determine one or more trends and/or for tracking purposes. For example, an upward or downward trend in number of patient records analyzed may be determined and/or tracked.

Metric(s) may be presented to a user (operation 520). For example, a metric GUI may be determined by the IMD system. A notification may be transmitted based on and/or including the metric. In some implementations, the metric(s) may be presented to the user, a designated user (e.g., Clinic head) and/or groups of users (e.g., via a transmitted notification and/or GUI(s) generated by the IMD system).

Report(s) may be generated based on the metrics (operation 525). For example, compliance with one or more industry and/or government standards may include transmission of reports of various metrics, such as number of patients test results analyzed. The IMD system may automatically determine metric(s) and/or automatically generated reports for compliance with industry and/or government standards (e.g., based at least partially on the determined metric(s) and/or criteria of the industry and/or government standards). The IMD system may automatically transmit the report(s) to the appropriate entity. In some implementations, the IMD system may automatically generate a compliance report, present the compliance report to a user (e.g., user associated with the compliance report and/or a department head), and/or automatically transmit the report(s) to the appropriate entity after receiving approval (e.g., via the GUI) from the user to which the report is presented.

A suggested set of reference materials may be determined based on the metrics (operation 530). In some implementations, the IMD system may generate a listing of references for presentation to the user based on determined metric(s). For example, the IMD system may determine metrics, such as accuracy and/or error rates, based on follow-up test and determine whether the metric is correlated to a specific area (e.g., associated with the selection or lack of selection of particular image icon(s)). The IMD system may then retrieve a suggested set of references related to the specific area (e.g., a set of references primarily and/or secondarily associated with image icon(s)). In some implementations, the IMD system may track metrics such that new areas of diagnoses for a user may be identified. The IMD system may generate a suggested set of reference materials based on the new areas of diagnoses. The IMD system may determine that a user is diagnosing using a statistically significant greater number of a particular image icon than other users, and may correlate the user error rate to suggest a set of references related to the image icon.

Image icon(s) selections may be correlated to outcome(s) (operation 525). For example, selections of image icon(s) may be aggregated from patient-de-identified data sets and correlated to outcomes (e.g., to comply with industry, government, and/or insurance regulations). For example, the IMD system may correlate follow-up information, such as outcomes (e.g., from biopsies, further testing, operative testing, and/or temporal follow-up), with diagnoses provided (e.g., via image icons selected) and determine probabilities of future outcomes based at least partially on the image icon or icons selected for the patient case in question.

Process 500 may be implemented by various systems, such as system 100. In addition, various operations may be added, deleted, and/or modified. For example, the determination of metrics, monitoring, and/or storage of information may comply with government, industry, and/or facility regulations, such as HIPAA (Health Insurance Portability and Accountability Act) and/or ACA (Affordable Care Act). In some implementations, the determined outcomes may be presented to user(s). In some implementations, the described process and/or operations thereof may be performed by the IMD system and/or an IMA system in other environments (e.g., forensic analysis, body imaging, and/or security screening).

Figure 6:
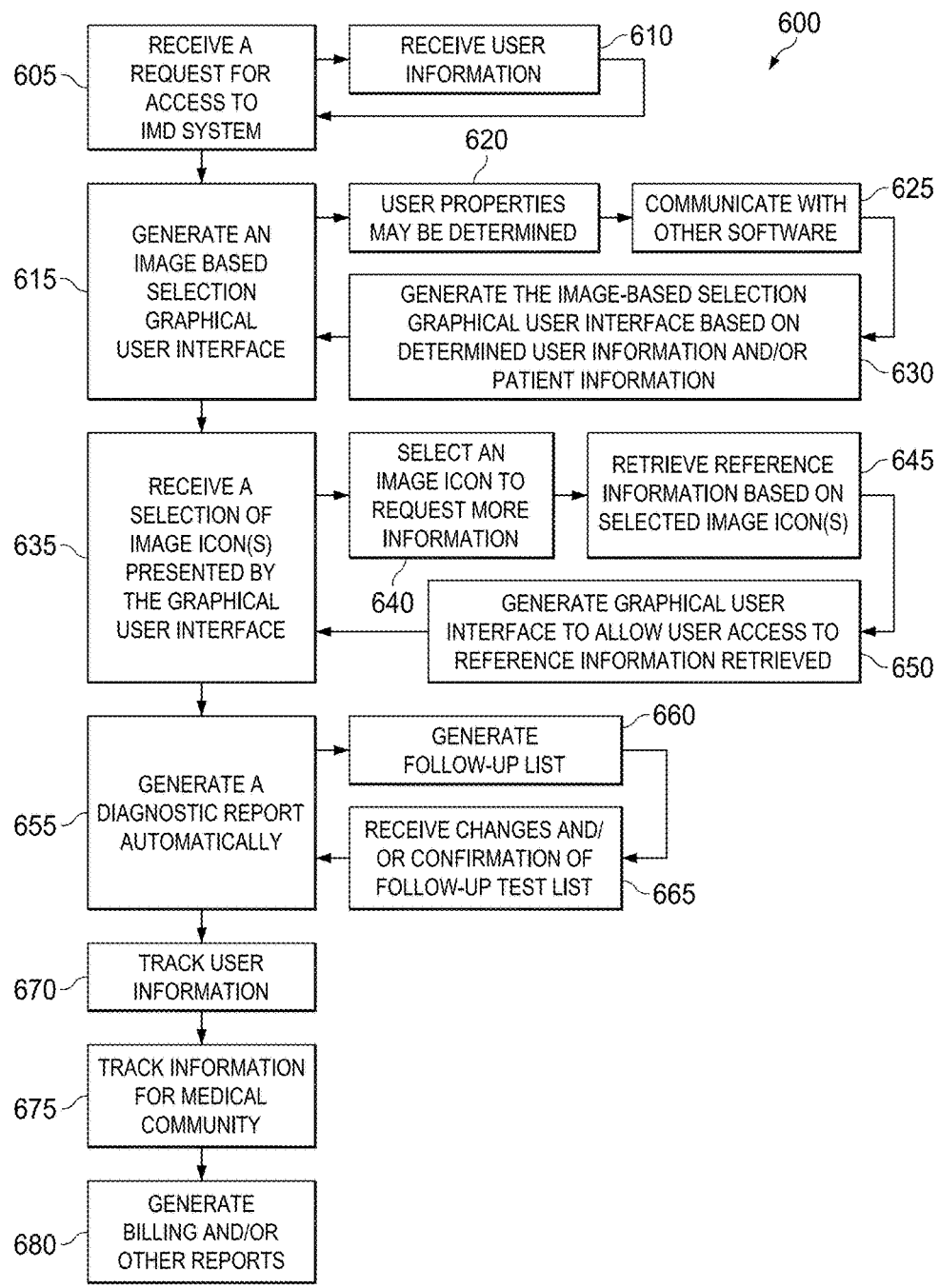
FIG. 6 illustrates an implementation of an example process for operating an image based medical diagnostic (IMD) system.

FIG. 6 illustrates an implementation of an example process 600 for operating an image-based medical diagnostic (IMD) system. A request may be received for access to an IMD system (operation 605). For example, a user may access a website that is a GUI generated by the IMD system. In some implementations, a portion of the presentation interface of the IMD system may be stored on a user device and/or access to the IMD system may be provided through the GUI generated by the portion of the presentation interface stored on the IMD system. The GUI may be a website accessed by the user.

User information may be received (operation 610). For example, a user may log into the IMD system by providing a user name and/or password. As another example, user information may be stored on a memory of the user device and the user information may be transmitted by the user device to the IMD system. The IMD system may compare the user information to user information in a memory of the IMD system to retrieve appropriate information (e.g., task lists, unconfirmed generated reports, statistics based on tracking, and/or notifications such as notification that user has satisfied regulatory requirements).

An image-based selection GUI may be generated (operation 615). For example, the diagnostic interface, reference interface, presentation interface and/or portions thereof may generate the image-based selection GUI.

User properties may be determined (operation 620). For example, specialty, assigned cases, and/or name and/or type of hospital that is serviced may be determined (e.g., from user records and/or user input). The user properties may indicate preferences for report generation, reporting requirements (e.g., government, industry, licensing, and/or research), and/or billing practices that may be utilized at least in part by the IMD system. In some implementations, the user properties may be retrieved based on the user information received to login to the IMD system.

The IMD system may communicate with other software, such as a third party interface for viewing patient test results (operation 625). For example, the IMD system may retrieve patient medical history. As another example, the IMD system may compare the patient identification information associated with the generated GUI for a patient with the patient information related to medical images generated by commercially available software, such as PACS/RIS/BRIS modules available from GE, Phillips, Siemens, McKesson (e.g., Magview module); Hologic (e.g., MRS module), and/or PenRad. In some implementations, the GUI may not retrieve and/or restrict presentation of medical images of a patient within the GUI.

The image-based selection GUI may generate the image-based selection GUI based on determined user properties and/or patient information (operation 630). For example, the image-based selection GUI may include image icons based on the medical cases to be analyzed and/or the types of tests that produced the medical images. The image-based selection GUI may include image icons based on the specialty of the physician. The image-based selection GUI may generate the GUI based on patent information such as reason for imaging. Other icons and/or tabs within the GUI may be presented on the image-based selection GUI based on the user properties and/or patient information.

A selection of one or more image icons presented by the image-based selection GUI may be received (operation 635). For example, a user may click, touch, and/or otherwise select an image icon on a user device, such as a tablet computer, and the information may be transmitted to the IMD system. The user may select one or more image icons to enter a diagnosis for a patient. Allowing the user to select an image to enter diagnosis, rather than dictating a diagnosis, may facilitate tracking since common diagnosis terms may be associated with the image icons for use in reports; can be assigned specific codes in the database; may be more cost efficient since users may be able to quickly enter diagnosis information; may reduce errors due to transcription of dictation; may reduce errors by providing reports approximately concurrently with diagnosing patients; and/or may be generally quicker for a user because as a user gains familiarity with the GUI and image icons, diagnoses may be quickly selected (e.g., when compared with the amount of time associated with having to repeat common diagnosis terms for each patient file when dictating).

A user may utilize the image-based selection GUI to request more information by selecting an image icon (operation 640). For example, if a user selects an image icon to request more information, the IMD system may retrieve reference information (e.g., via the reference interface and/or by retrieving information by accessing repositories) (operation 645). The reference information may be indexed based on images (e.g., image icons) and/or other icons and thus by selecting an icon, information that may be relevant to diagnosing and the image in the icon may be viewed. In some implementations, users may flip through a plurality of images in the reference information to facilitate a formulation of a diagnosis.

The image-based selection GUI may be generated so that the user may access reference information retrieved (operation 650) and/or view reference information correlated (e.g., through the index) to the selected image. For example, if a user is unsure that a possible diagnostic term (e.g., image icon and/or other icon) accurately reflects at least a portion of a patient medical image, a user may select the possible diagnostic term image icon and access reference information related to the icon. Thus, a user may access reference information that may be relevant to diagnosing based on a possibly similar image rather than search terms and as such may be able to retrieve reference information without knowledge of appropriate search terms, in some implementations.

A diagnostic report may be automatically generated (operation 655). For example, the IMD system may utilize the selected image icons to formulate the diagnosis in words for transmission to a patient and/or referring physician. The diagnostic report may be generated based at least partially on common terms in the field and/or uniform diagnostic terms. For example, governments, medical boards, hospitals, and/or insurers may require diagnostic reports to utilized specified uniform diagnostic terms. The IMD may retrieve the specified uniform diagnostic terms and generate the patient report at least partially based on the retrieved terms. The report may also be generated at least partially based on retrieved patient information (e.g., from interfacing with other commercially available software). The report may be text and/or image searchable.

Generating text and/or image searchable reports may facilitate compliance with government regulations, industry recommendations, and/or research endeavors.

Other reports may be automatically generated. For example, a follow up test list may be generated (operation 660). A potential follow up test list may be generated by the system at least partially based on icons selected in the GUI and/or other information (e.g., based on common practices in industry, based on hospital preferences, insurance preferences, and/or based on user preferences). Changes and/or confirmation by a user of a generated list of follow up tests may be received (e.g., from a user device) (operation 665). The follow up test list and/or other reports may be automatically transmitted to as appropriate (e.g., to electronic medical record, to physicians, to patients, to medical testing laboratories, etc.).

Information about the user may be tracked (operation 670). For example, regulations may require specific information to be tracked (e.g., to comply with confidentiality requirements, to maintain licensing, to manage business goals, to track efficiency). For example, a radiologist reading mammography may need to track, report, and/or confirm that a predetermined number of mammography records have been read by a user in a specified time. For example, the IMD system may retrieve a predetermined compliance value and compare the value to the number of cases read by the user and determine if a compliance value has been satisfied.

The information may be tracked for the medical community (operation 675) and a report may be generated. Reports based on the tracked information may be generated and/or transmitted (e.g., via email and/or printed) to appropriate other parties (e.g., regulatory boards, hospitals, etc.). For example, a compliance form may be retrieved form a repository and tracked information may be added to the retrieved form. As another example, a nuclear medicine radiologist may be required to comply with various regulations (e.g., government regulations regarding nuclear material, etc.) that would be automatically tracked by the IMD system. In some implementations, user efficiency and/or the efficiency of a group of users (e.g., number read, time required to read, and/or mistakes made) may be tracked and/or reports may be generated for business goals.

Other information related to diagnoses generated (e.g., through the selection of image icons) may be tracked. For example, the CDC or FDA may require reporting of specified diagnosis and/or prevalence of specified diagnosis. The IMD may automatically track and/or report the information to automatically comply with the requirement.

One or more other reports and/or billing reports may be generated (operation 680). For example, reports, such as compliance reports, metric reports, etc. may be generated. A billing report may be generated based at least in part on the image icon(s) selected. For example, CPT and/or ICD-9 codes may be correlated to image icons and billing reports may be automatically generated based at least partially on the selection of image icons.

Process 600 may be implemented by various systems, such as system 100. In addition, various operations may be added, deleted, and/or modified. For example, tracking of patient information and/or portions of patient information (e.g., to comply with regulations such as HIPPA) may be inhibited. As another example, the GUI may have default settings. The default settings may be based on user preferences and/or industry preferences. In some implementations, the described process and/or operations thereof may be performed by the IMD system and/or an IMA system in other environments (e.g., forensic analysis, body imaging, and/or security screening). Although FIGS. 2A-6 illustrate implementations of processes performed by the IMD system, similar processes and/or portions thereof may be performed by the IMA system, independently and/or in combination with one or more other processes and/or portions thereof, as appropriate.

In some implementations, the IMD system may receive and/or retrieve other information. Other information may include pathology from biopsies, results at follow-up, information from electronic medical records, location information and/or measurements related to images and/or occurrences, and/or other appropriate information from image presentation systems such as PACS, other computer aided diagnostic systems, and/or other appropriate systems. The other information may be retrieved automatically from other commercially available software systems by the IMD system and/or input by a user and transmitted to the IMD system.

The system may utilize the other information for compliance with various governmental agency requirements (e.g., Mammography Quality Standards Act [MQSA]) and/or business practice requirements (e.g., billing and/or uniform reporting). For example, a governmental agency may require tracking and/or correlating of various data (e.g., analysis, follow-up recommendations, and/or test results). The IMD system may track and/or generate report(s) based on the tracking and/or correlating. The tracked information may be utilized to create probability of diagnoses and/or malignancies based on diagnoses received through the system (e.g., the system may aggregate diagnoses and/or test results to determine probabilities of malignancy based at least in part on the aggregated information).

In some implementations, the system may present (e.g., through a GUI) a probability of an outcome for a selected image icon(s), other icon(s), and/or selected diagnoses. For example, the system may generate a probability of a diagnosis using the other information received by the system. The system may track and/or correlate selection(s) of image icon(s), other icon(s), and/or test results (e.g., pathology results such as biopsy results). The system may then be able to determine a probability of an outcome (e.g., malignancy) based at least in part selected icons. The system may utilize other information (e.g., from other commercially available software, such as electronic medical record information) when determining correlations and appropriate probabilities between selected icon(s) (e.g., image icons and/or other icons) and outcomes.

The results information (e.g., at follow-up and/or biopsy results) may be aggregated and/or correlated to diagnoses selected and various statistical models may be utilized to generate probabilities (e.g., of outcomes). In some implementations, the probability information may be determined from expert opinions (e.g., input into the system) and/or from other reference materials. The probability information may be stored in a memory of the system and/or in remote repositories. The system may receive a selection of image icon(s) and/or other icon(s) and retrieve a correlated probability based at least in part on the received selections. The probability information may be presented to a user and/or included in reports generated by the system (e.g., probability of malignancy may be included in diagnoses reports and/or the billing code selected may be at least partially based on the probability information).

For example, when a user analyzes a breast image and the user selects an image icon correlated to BI-RADS 4a, a probability of malignancy of 2-10% may be indicated by the system. As another example, a user may analyze an image and the user may select a diagnosis by selecting image icon(s) and/or other icon(s) through the GUI. The system may retrieve probability information (e.g., related to the selected image icon(s) and/or other icon(s)) and present the probability information to the user. The probability information may be at least partially based on the other information retrieved by the system. The system may generate a GUI, such as a pop-up window, that presents at least a portion of the probability information to the user. The GUI may, for example, indicate various things to the user, such as the rarity of the diagnosis selected by the user, the malignancy rate of the occurrence, and/or other probability related information. The user may alter the selection of image icon(s) and/or other icon(s) based at least in part on the probability information, in some implementations. For example, the user may select various follow-up tests based on the probability information and/or the user may re-examine the images and alter a diagnosis based on the probability information. Report(s) generated by the system may include information at least partially based on the probability information (e.g., probability information may be included for compliance with government reporting requirements).

In some implementations, the probability information may be utilized to determine if one or more users is selecting the appropriate icon related to a category (e.g., BI-RAD® or other level of suspicion). For example, if a level of suspicion is related to a 5% or less malignancy outcome and a user's selection of the category is correlated to an approximately 20% malignancy outcome, then the user may be notified of the discrepancy. In some implementations, a reporting agency may be notified when a plurality of user designate a category with an outcome (e.g., percentage of malignancy found) that is different from the outcome the reporting agency and/or other in the industry associate with the category.

In some implementations, other information received and/or retrieved by the IMD system may include location information (e.g., location within the anatomical region, size, signal characteristics such as T1, T2, STIR (Short Tau Inversion Recovery), contrast enhancement (CE), dynamic contrast enhancement (DCE), DWI (diffusion weighted imaging), and/or DTI (diffusion tensor imaging) for MRIs. The location information may be input by a user while obtaining the image (e.g., an ultrasound technician may enter location information). In some implementations, commercial image analysis systems may allow location information such as measurements and position to be obtained through the commercial image analysis system. For example, the user may be able to measure a location of an occurrence (e.g., lesions) through the system through which the user views the x-ray.

The IMD system may generate one or more GUIs to facilitate interaction, receipt of information, and/or presentation of information to user(s), FIGS. 7-15 illustrate implementations of example GUI(s) generated by the IMD system. The GUI(s) may be presented on a user device, for example, through a website and or via a local site. Access to the GUI(s) and/or information therein may be secured (e.g., to ensure compliance with one or more government and/or industry standards). The GUI(s) may include a home-screen (e.g., preset home-screen and/or based on user preferences) and tabs corresponding to one or more other GUIs, such as diagnostic GUI(s) including abbreviated diagnoses GUI(s) and other diagnoses GUI(s), report GUI(s), work-list GUI(s), etc.

During use, a user such as a radiologist, may access the IMD server through a GUI (e.g., logon GUI) generated by the IMD server. The radiologist may view the GUI(s) generated by the IMD server on a first user device, such as a tablet computer, and view medical images of a patient (e.g., patient test results) on additional user device(s). In some implementations, the user may view medical images, such as ultrasounds and CT scans, on one more monitors coupled to the additional user device(s) and view the GUI generated by the IMD system on another monitor coupled to the user device and/or screen of a tablet computer, as illustrated in FIG. 1. The medical images of the patient may be retrieved using commercially available medical image software (e.g., third party systems, as illustrated in FIG. 1). The IMD system may interface with the medical image software to ensure diagnostic information entered through the GUI is correlated to the medical images presented by the medical image software. For example, the IMD system may request patient information from the medical image software and generate GUIs based on the patient information. The IMD system may allow a user to input patient identification information (e.g., scan a barcode, type a number) into the generated GUI and retrieve information about the associated patient based on the input patient identification information and/or transmit a request to the medical image software for confirmation of the patient identification information.

Figure 7A:
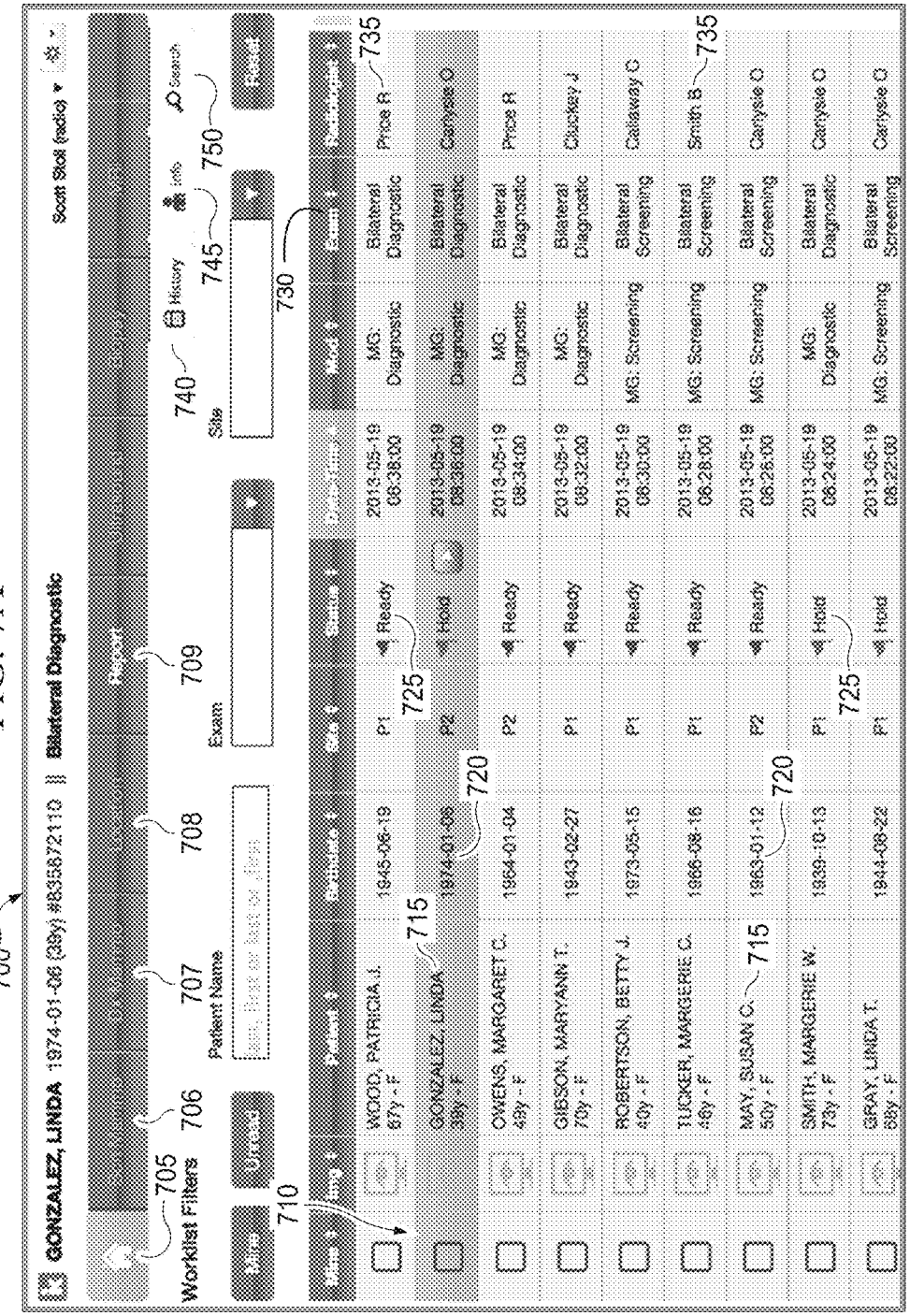
Figure 7B:
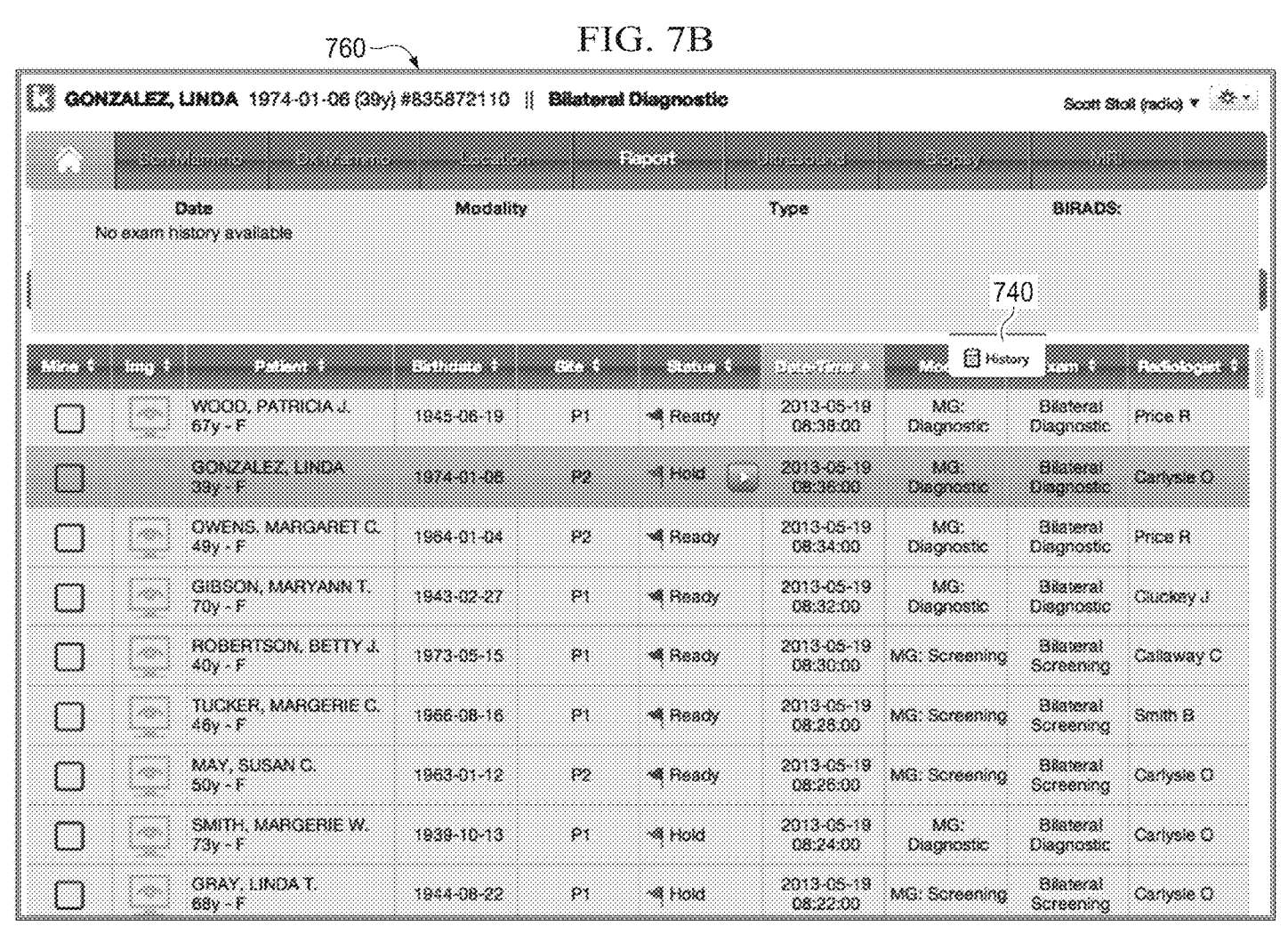

In various implementations, the IMD system may generate a work-list GUI. FIG. 7A illustrates an implementation of an example work-list GUI 700. A user may access the IMD system (e.g., via the Internet) and provide one or more credentials, such as user names and/or passwords. The IMD system may generated a work-list GUI as illustrated in FIG. 7A, based at least partially on the provided credentials. As illustrated, the work-list GUI 700 may be accessible to a user by selecting a tab on the interface, such as a home-screen tab 705. A listing 710 of one or more patients, with whom test results are associated, may be included in the work-list GUI 700. The listing 710 may include patient record information such as patient name 715; identifying information, such as birth date 720; status and/or status indicia 725, type of examination 730, and/or username 735 or other user information related to a user assigned to evaluate test results associated with the patient record. Additional information about a selected user may be presented to a user via one or more tabs, such as exam history tab 740 and/or patient information tab 745. FIG. 7B illustrates an example of a work-list GUI 760 in which the exam history tab 740 has been selected for presentation.

Figure 7C:
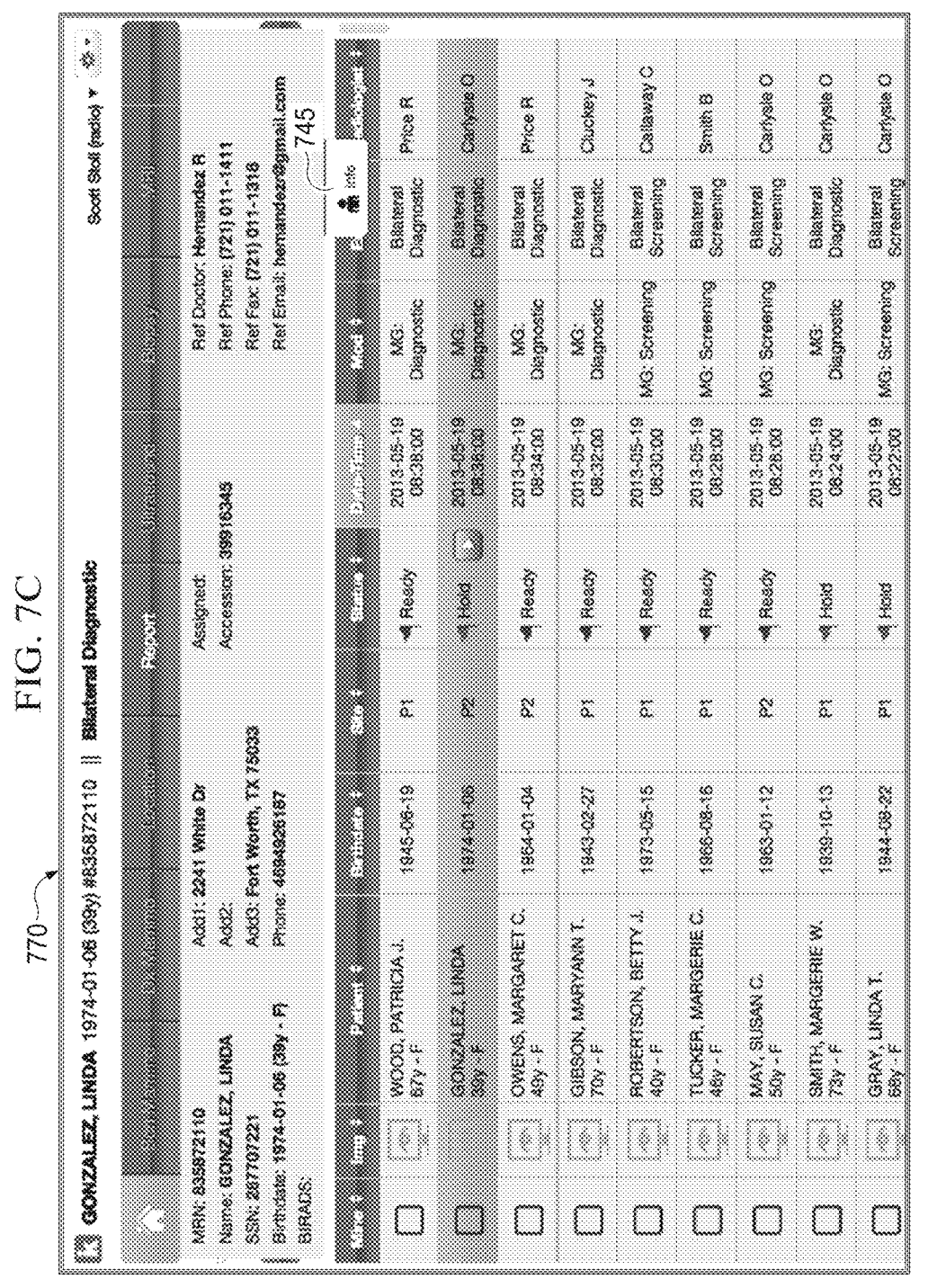
Figure 7D:

In some implementations, the IMD system may communicate with one or more third party systems to determine the additional information, such as exam history, patient history, medical record information, etc. For example, the IMD system may pull examination history from an electronic medical record stored in a memory (e.g., database) coupled to the IMD system. FIG. 7C illustrates an example of a work-list GUI 770 in which the patient information tab 745 has been selected for presentation. A user may search for information such as a patient record via a search tab 750. FIG. 7D illustrates an example of a work-list GUI 780 in which the search tab 750 has been selected for presentation.

As illustrated in FIG. 7A, the GUI(s) generated by the IMD system may include tabs that allow the user to request presentation of various GUIs. For example, the GUI(s) may include a home-screen tab 705; one or more diagnoses GUIs presented through one or more diagnoses tabs, such as an abbreviated diagnosis tab 706 and/or a diagnosis tab 707; a location tab(s) 708; and/or report tab(s) 709.

In some implementations, tabs may allow presentation of GUIs that include information such as task lists that include assigned cases, generated reports, and/or custom screens. The user may customize a custom screen by inputting user preferences (e.g., user tracking data including number of cases read, efficiency, and/or billing reports). The tabs may also include various tabs that relate to different types of medical images that may be viewed and/or analyzed by the user. For example, a <Dx Mammo> tab may generate an interface that allows entry of a diagnosis (e.g., by selection of image icons and/or other icons) related to a mammography case. An <Ultrasound> tab may generate an interface that allows entry of a diagnosis (e.g., by selection of image icon(s) and/or other icons) related to the analysis of an ultrasound. A <Screen Mammo> tab may generate a home page or initial starting point page for selection of image icons and/or other icons related to a diagnosis.

In some implementations, a user may select a patient from the work-list GUI 700 and then select a diagnoses GUI through a diagnosis tab. The diagnostic GUI may include image icon(s). The image icon(s) may include at least a portion of a photographic image, such as a medical image (e.g., CT scan and/or ultrasound). The photographic image selected for inclusion in the image icon may be a typical, exemplary, and/or common occurrence of a diagnosis or portion thereof. For example, a cyst may typically present in a CT scan in a similar manner as a first photographic image. The first photographic image or portions thereof may be included in a characteristic image icon for a cyst.

In some implementations, the IMD system may include more than one diagnostic GUI, in some implementations. For example, diagnosis GUIs may include abbreviated diagnostic GUI(s); one or more specialized diagnosis GUI(s), such as MRI diagnostic GUI(s), ultrasound diagnostic GUI(s), and/or body imaging GUI(s); and/or other diagnostic GUI(s). In some implementations, an abbreviated diagnostic GUI may be available with fewer image icons than a non-abbreviated diagnostic GUI. The abbreviated diagnostic GUI may allow a user to quickly provide a selected set of diagnoses. For example, the abbreviated diagnostic GUI may allow a user to quickly select a benign diagnosis or BI-RADS® 0 Category of assessment.

Figure 8A:
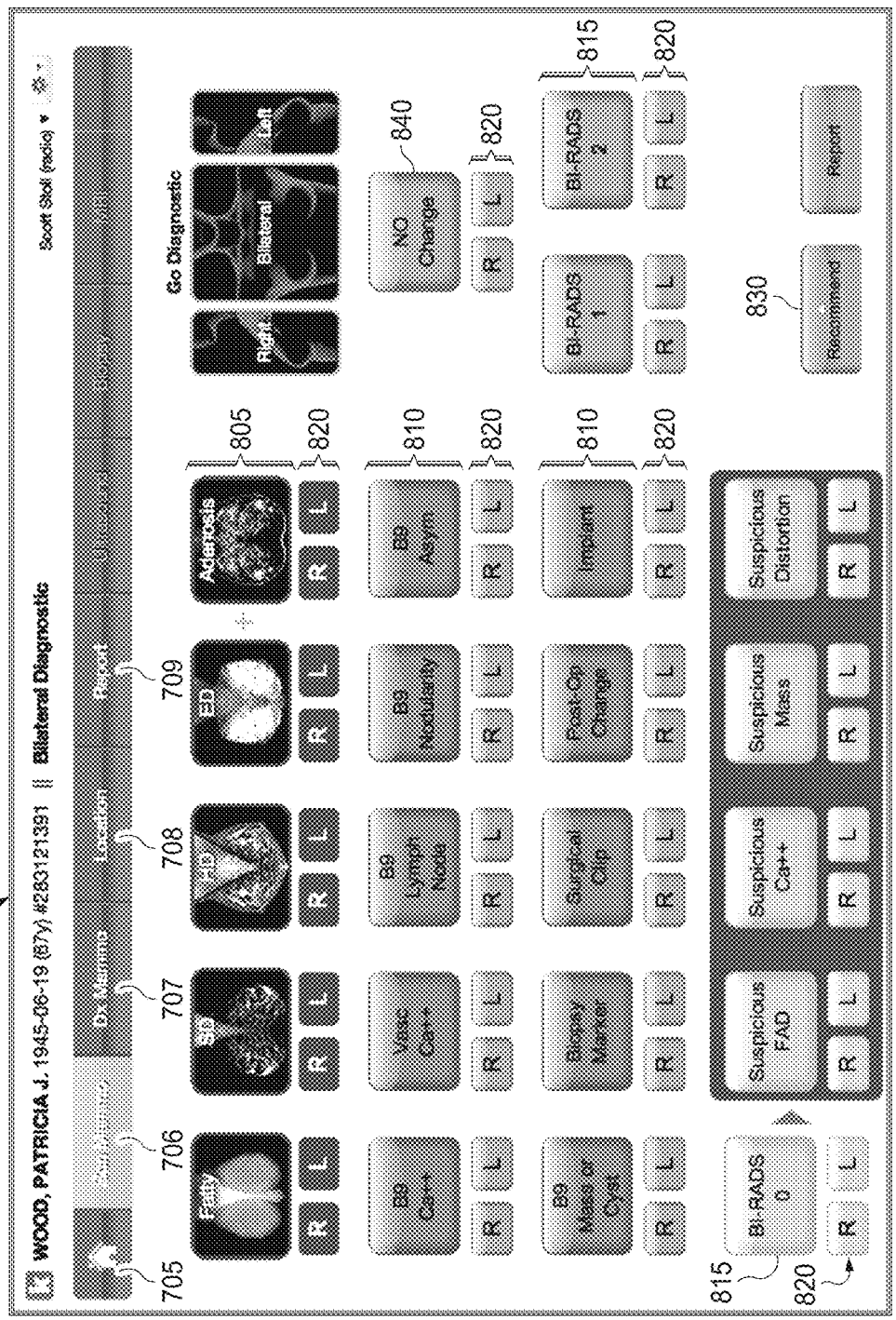
FIG. 8A illustrates an implementation of an example abbreviated diagnosis graphical user interface.
Figure 8B:
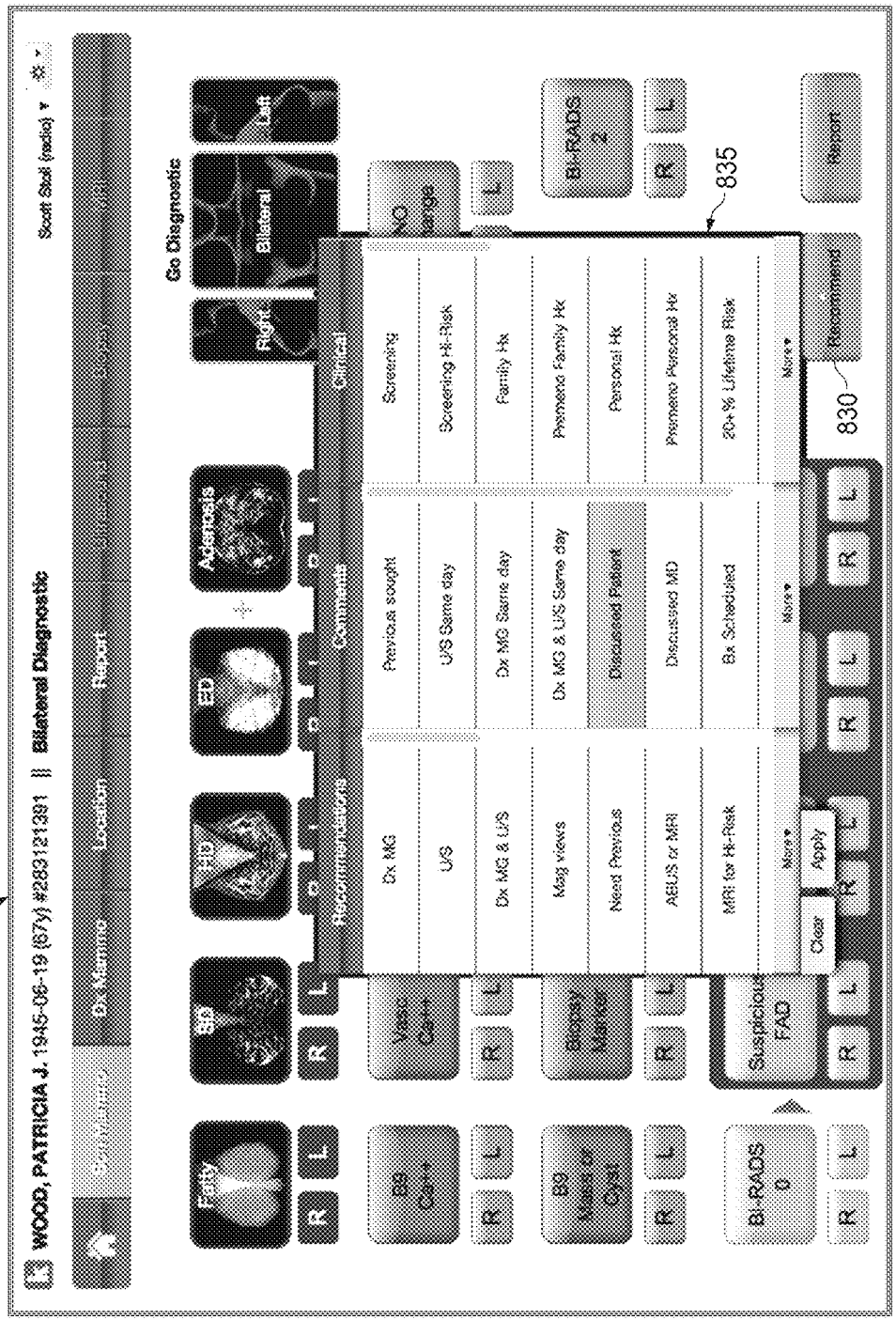
FIG. 8B illustrates an implementation of an example abbreviated diagnosis graphical user interface.

FIG. 8A illustrates an implementation of an example of an abbreviated diagnostic GUI 800 generated by the IMD system. In some implementations, after a user selects a patient form a work-list, a user may select the abbreviated diagnostic GUI though which diagnosis information related to the selected patient and/or test results of the patient may be provided. In some implementations, a user may select the abbreviated diagnosis tab 706 to request presentation of the abbreviated diagnostic GUI 800. The abbreviated diagnostic GUI 800 may include one or more image icons. As illustrated, the diagnostic GUI 800 includes characteristic image icons, such as breast density image icons 805. In some implementations, each breast density image icon 805 may correspond to a different level of breast density. As illustrated, the breast density image icon(s) 805 may include text (e.g., abbreviations of diagnoses) that is related to the photographic image in the breast density icon. The user may request variations of an image icon (e.g., by double-click the image icon, by selecting the image icon and one other text icon, and/or by selecting image icon(s) and requesting variation information). The IMD system may retrieve one or more images and/or image icons depicting variations of the characteristic in the image icon selected. For example, if variations of a fatty breast density image icon is requested by a user, then the IMD system may retrieve variations of fatty breast density (e.g., examples of different presentations of fatty breast density). Selection among two or more image icons may be facilitated by presenting variations to the user. For example, if the patient test results include breast imaging and the user is unsure which categorization of breast density the patient test results fall within, then presentation of variations facilitate selection of the categorization. In some implementations, a third party system may pre-screen patient test results to determine breast density and indicia may be presented on the diagnostic GUI breast density image icon proximate the breast density category determined by the pre-screening. The user may then confirm the breast density category and/or alter the category (e.g., by selecting a different image icon).

The abbreviated diagnostic GUI 800 may include one or more text icons, such as text diagnosis icons including characteristic text icons 810 and/or BI-RAD text icons 815. The text diagnosis icons 810 included in the abbreviated diagnostic GUI 800 may be a preselected set of the text diagnosis icons included in a non-abbreviated diagnostic GUI 800.

In some implementations, an anatomical location corresponding to a selected image and/or text icon may be selected. The abbreviated diagnostic GUI 800 may include text icons, such as anatomical location text icons 820, selection of which may indicate a location of a patient corresponding to a selected image icon(s) and/or diagnosis text icon(s). In some implementations, the abbreviated diagnostic GUI 800 may include an anatomical location graphic 810 through which an anatomical location may be provided.

The abbreviated diagnostic GUI 800 may include icons 830 that when selected allow a user to provide additional information for inclusion in the diagnostic report and/or the patient record. As illustrated in the interface 850 illustrated in FIG. 8B, when an icon 830 is selected, recommendations may be provided through an additional information interface 835 generated by the IMD system. The additional information interface 835 may allow recommendations, comments, follow-up tests and/or other additional information to be provided by a user (e.g., through selection of fields). In some implementations, the abbreviated diagnostic GUI 800 may include a text icon to indicate whether a change has occurred since a previous test result 840.

Figure 9A:
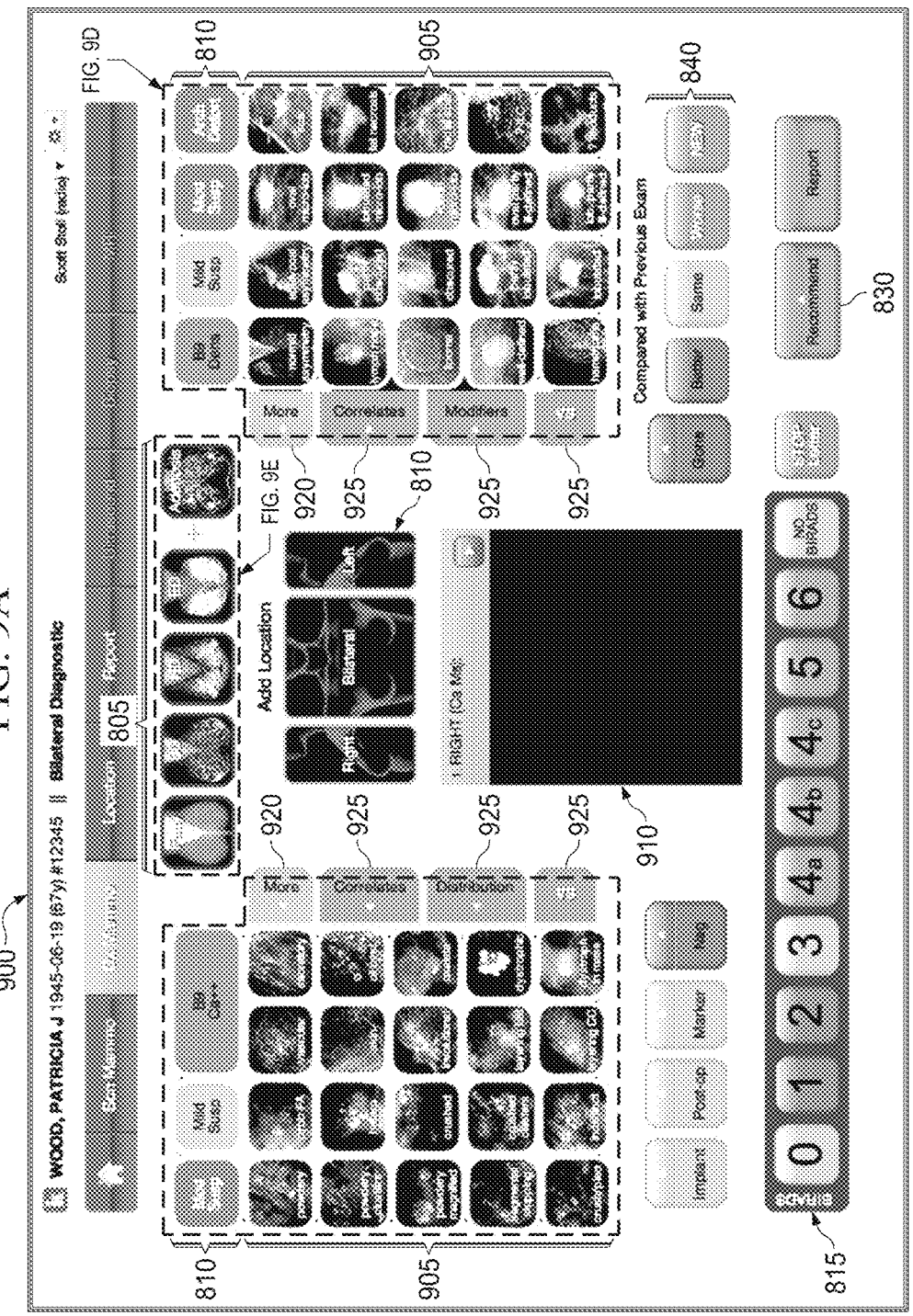
FIG. 9A illustrates an implementation of an example diagnosis graphical user interface.
Figure 9B:
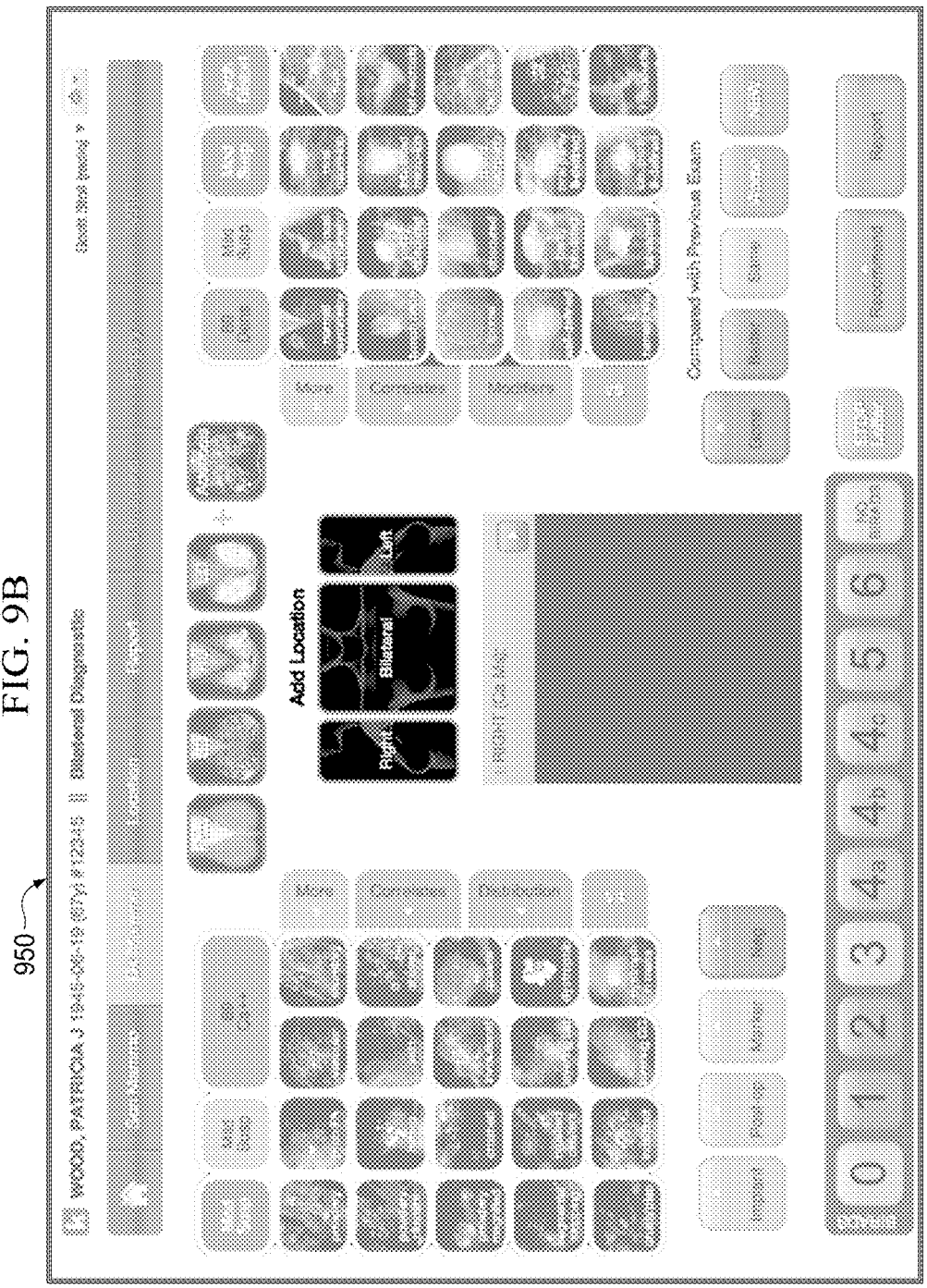
FIG. 9B illustrates an implementation of an example diagnosis graphical user interface in which selection of one or more icons is restricted.
Figure 9C:
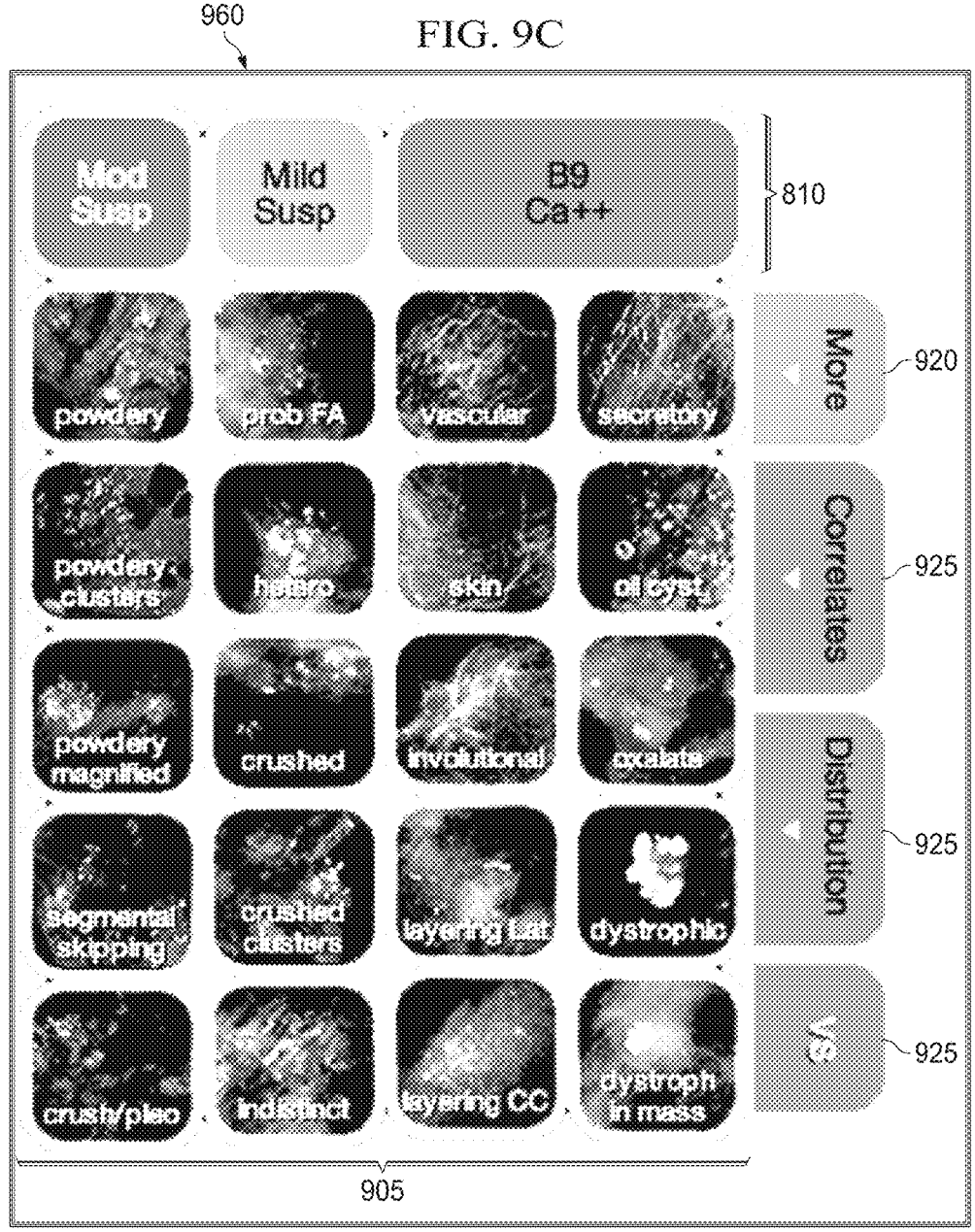
FIG. 9C illustrates an implementation of a portion of the example diagnosis graphical user interface illustrated in FIG. 9A.
Figure 9D:
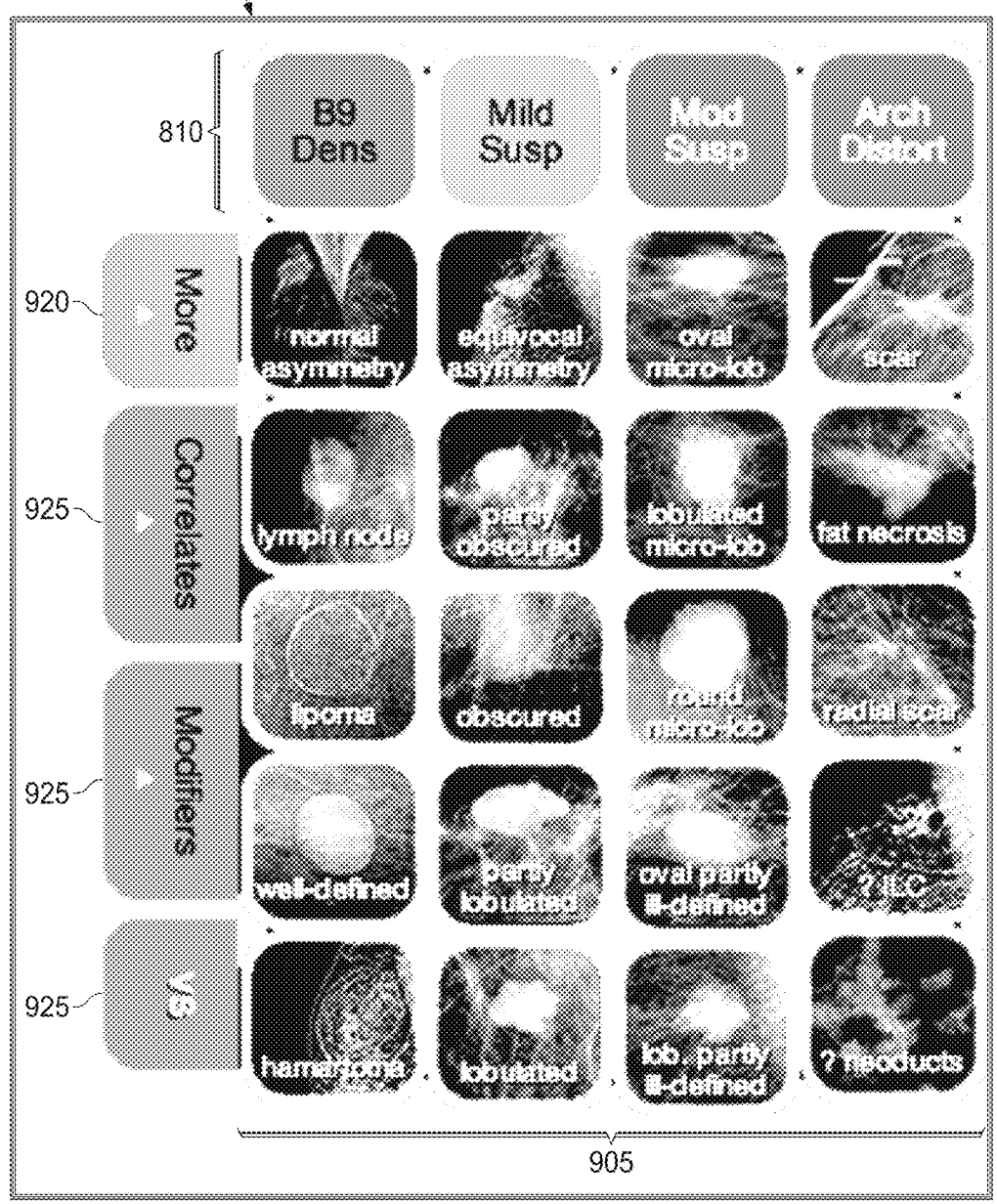
FIG. 9D illustrates an implementation of a portion of the example diagnosis graphical user interface illustrated in FIG. 9A.
Figure 9F:
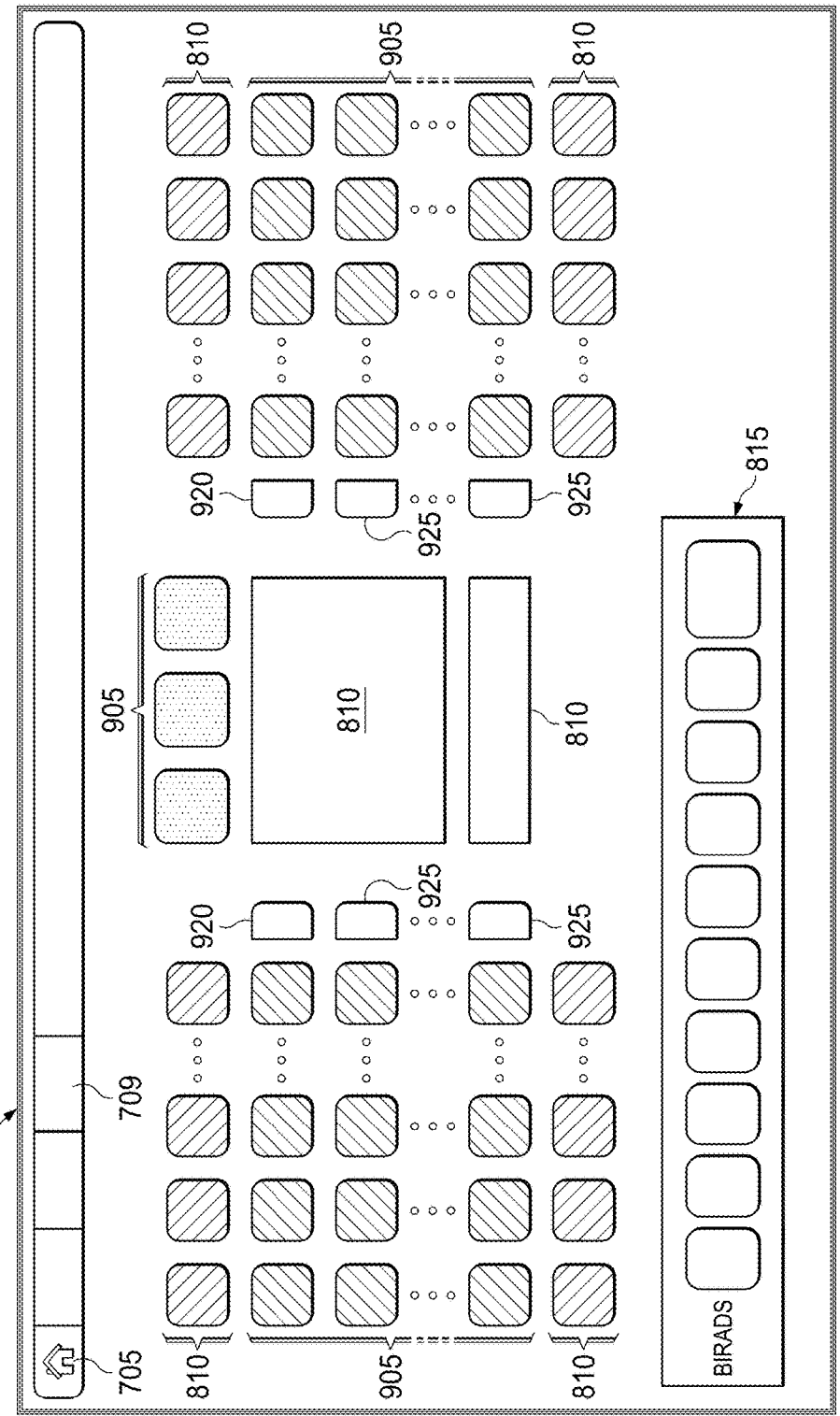
FIG. 9F illustrates an implementation of an example diagnosis graphical user interface.

In some implementations, a user may select a diagnostic GUI with more image icons than available through the abbreviated diagnostic GUI (e.g., thus, more detail and/or diagnoses may be provided compared to the abbreviated diagnostic GUI). For example, a user may select a diagnosis tab 707 through a GUI of the IMD system. In some implementations, the user may select a patient and the IMD system may communicate with a third party system to ensure that the selected patient corresponds to the patient test results being presented to the user through the third party system. The IMD system may generate a diagnosis GUI based at least partially on a selected patient, the test results presented through the user via a third party system, patient electronic medical records, etc. FIG. 9A illustrates an implementation of an example diagnostic GUI 900 generated by the IMD system. FIGS. 9B, 9C, and 9D illustrate different portions of the example diagnostic GUI illustrated in FIG. 9A. FIG. 9E illustrates a schematic of an implementation of an example diagnostic GUI 900 generated by the IMD system.

As illustrated in FIGS. 9A-E, the diagnostic GUI 900 may generate and/or present image icons including characteristic icons, such as breast density image icons 805 and/or lesion characteristic icons 905, and/or other icons. As illustrated, the image icons may include at least a portion of a medical photographic image of an example of a characteristic. The image icon may include at least a portion of a photographic image of the presentation of a characteristic (e.g., an example of a presentation of a characteristic). The image of the presentation of a characteristic (e.g., as a typical presentation) may be selected by an administrator, such as an expert in the field. For example, the image icon may include a portion of an MRI of an aneurism, a portion of a radiograph of a mass, etc. The image icons may include text that describes the characteristic illustrated in the image icons. For example, an image icon that includes at least a portion of a medical photographic image of powdery calcification may include text such as "powdery" and/or an image icon that includes a medical image of well-defined mass may include text such as "well-defined". For example, rather than including line drawings or other representations of characteristics, the IMD system may utilize image icons that include photographic images. The use of photographic images in image icons may increase the ease of use of the IMD system for users, since the user does not have to translate what the drawing of a characteristic actually looks like in a patient test result. In some implementations, the user of photographic images may allow and or aid a user in the identification of unknown characteristics. For example, if the user identifies a characteristic in a patient test result, but does not know the name of the characteristic, then the user may identify the characteristic based on the photographic image in the image icon on a GUI of the IMD system. In some implementations, a characteristic in a patient test result may not closely resemble image icon(s) in the GUI and the user may utilize the photographic images of variations retrievable by the system to identify the characteristic based on the images.

As illustrated, the diagnostic GUI 900 may include one or more text icons, such as diagnostic text icons 810 and/or BI-RAD or other categorization text icons 815. The diagnostic text icon may be associated with at least a portion of the diagnosis. For example, a diagnostic text icon may indicate a level of suspicion and/or other information related to a diagnosis or portion thereof (e.g., a benign calcification, a surgical clip, a biopsy marker, an implant, mass, cyst, post-operative change). The other categorization text icons may include a size text icon 920. The size text icon 920 may control the number of image icons presented through a diagnostic GUI 900. For example, a size text icon 920 may be to cause a greater number of image icons to be displayed (e.g., by selecting a <more> size text icon) and/or may cause fewer image icons to be displayed (e.g., by selecting a <less> size text icon).

In some implementations, the number of image icons and/or text icons presented on the diagnostic GUI 800, 900 may be based on the user device, type of user device, presentation device size (e.g., screen size), user preferences, etc. For example, the IMD system may automatically determine the number of image icons and/or text icons to include in a generated GUI based on the user device and/or properties thereof (e.g., screen size). A user may request alteration of the number of image icons and/or text icons presented in the generated GUI, for example, by selecting a size text icon, such as the size text icon 920 illustrated in FIG. 9A. The IMD system may receive the request to alter the number of image icons and/or text icons (e.g., by selection of a size text icon) and alter the number of image icons and/or text icons included in the generated GUI.

The diagnostic GUI 900 may include one or more other icons that allow comparisons to previous test results 840 and/or other additional information 830.

The diagnostic GUI 900 may allow a user to provide location information, such as an anatomical location of a patient (e.g., corresponding to an anatomical location in the test results of the patient). As illustrated, the diagnostic GUI 900 may include an anatomical location graphic 810 and/or other portion 910 to allow a user to select and/or provide an anatomical location to be associated with the patient record. The anatomical location graphic 810 may be an image and/or a drawing of at least a portion of a body. A user may be able to select an anatomical location through the anatomical location graphic 810. For example, indicia (e.g., a dot, a circle, a flag) may be placed on a portion of the anatomical location graphic 810 to provide an anatomical location (e.g., to the IMD system to be associated with a patient record).

In some implementations, the IMD system may restrict and/or allow selection of various icons based on predetermined preferences, user preferences, industry preferences, etc. For example, selection of one or more image icons may be restricted until a selection of an anatomical location is received. FIG. 9B illustrates an example diagnostic GUI 950 in which selection of image icons is restricted. As illustrated, the image icons are grayed or hidden to indicate that the icons may not be selected. In some implementations, a user may not be restricted in which icons may be selected.

In some implementations, during use, a user may select a patient from a work-list GUI 800. The IMD system may communicate with a third party system through which patient test results are retrieved for presentation on a user device. The IMD system may communicate with the third party system such that the patient test results being presented to the user via the third party system are associated with the same patient and/or record as the patient record in which a diagnosis will be entered through the IMD system. The user may then select a diagnostic GUI 800, 900 though which a diagnosis may be provided by the user. For example, the user may view the medical images from patient tests, such as mammography, and view the icons in the GUI of the IMD system. The user may select image icon(s), such as lesion characteristic icons 905, that correspond to the analysis of the patient test results presented to the user. The user may select an anatomical location (e.g., via a anatomical location graphic 810) and/or other icons, such as diagnosis text icons 810, BI-RAD text icons 815, icons to provide comparisons to previous test results 840, additional information icons 830, and/or association icons 925.

The association icon(s) 925 may allow a user to indicate a relationship between selected image icons. For example, association icon(s) may be text icons that indicate that image icons are correlated (e.g., "and" and/or "or"), distribution, modifiers, pertinent negative diagnosis (e.g., "not"), and/or to provide differential diagnosis information (e.g., 'vs.' icon). In some implementations, the user may select more than one image icon via the diagnostic GUI 800, 900 and one or more association icons 925 to indicate the relationship between the selected icons. Users may thus select that certain diagnoses or portions of diagnoses correlated to image icons are present and/or not present in the patient medical images and/or specific anatomical locations of such being analyzed by the user. The inclusion of negative diagnosis information may provide additional information to the generated diagnosis based on selected image icons for other physicians, for example, in the generated report.

Figure 10:
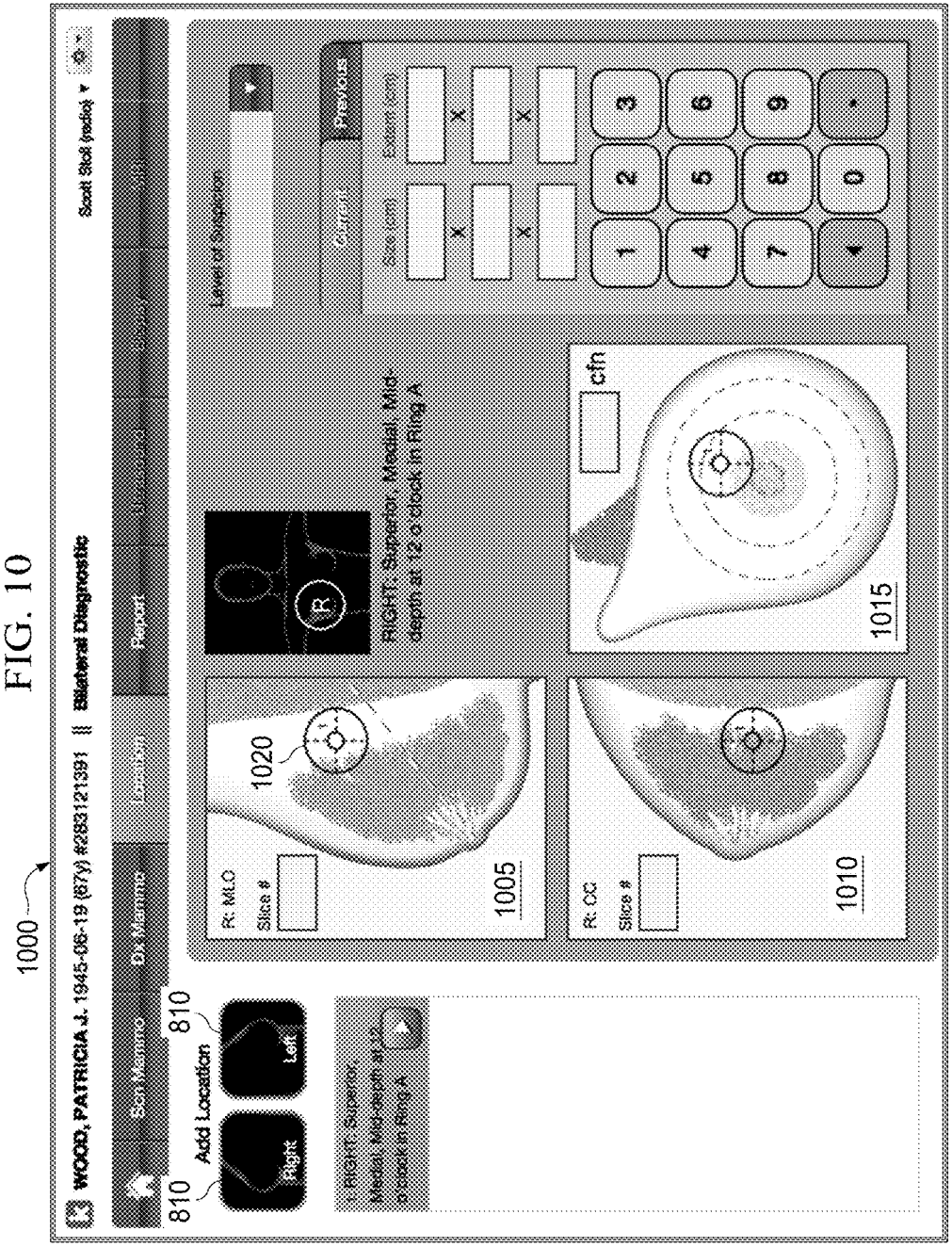
FIG. 10 illustrates an implementation of an example location graphical user interface.

In some implementations, location GUI(s) may be generated by the IMD system through which a user may provide anatomical location(s). FIG. 10 illustrates an implementation of an example location GUI 1000. The location GUI 1000 may include one or more graphical images (e.g., line drawing) that illustrate a representation of a patient or portion thereof. For example, as illustrated, the location GUI 1000 may include graphical images that illustrate different views of a breast 1005, 1010, and 1015. A user may position a location indicator 1020 on one or more of the views 1005, 1010, and 1015 to provide an anatomical location. The location GUI may include an anatomical location graphic 810, to, for example, indicate to which side of a patient's body a positioned location indicator corresponds. A diagnosis corresponding to the anatomical location may be provided through a diagnostic GUI 800, 900. In some implementations, a level of suspicion may be provided.

In some implementations, the location GUI(s) may be automatically generated by the IMD system based on patient test results, user properties (e.g., belongs to mammography group and/or body imaging group), and/or user selections (e.g., user provides anatomical location included in the patient test results). For example, when an MRI of a breast is included in the patient test results, the IMD system may automatically generate a location GUI that includes images of the breast. In some implementations, when a radiograph of an arm is included in the patient test results, the IMD system may automatically generate a location GUI that includes images of an arm. The image illustrated in the GUI may be a representation of an anatomical location rather than the image in the patient test results.

Figure 11:
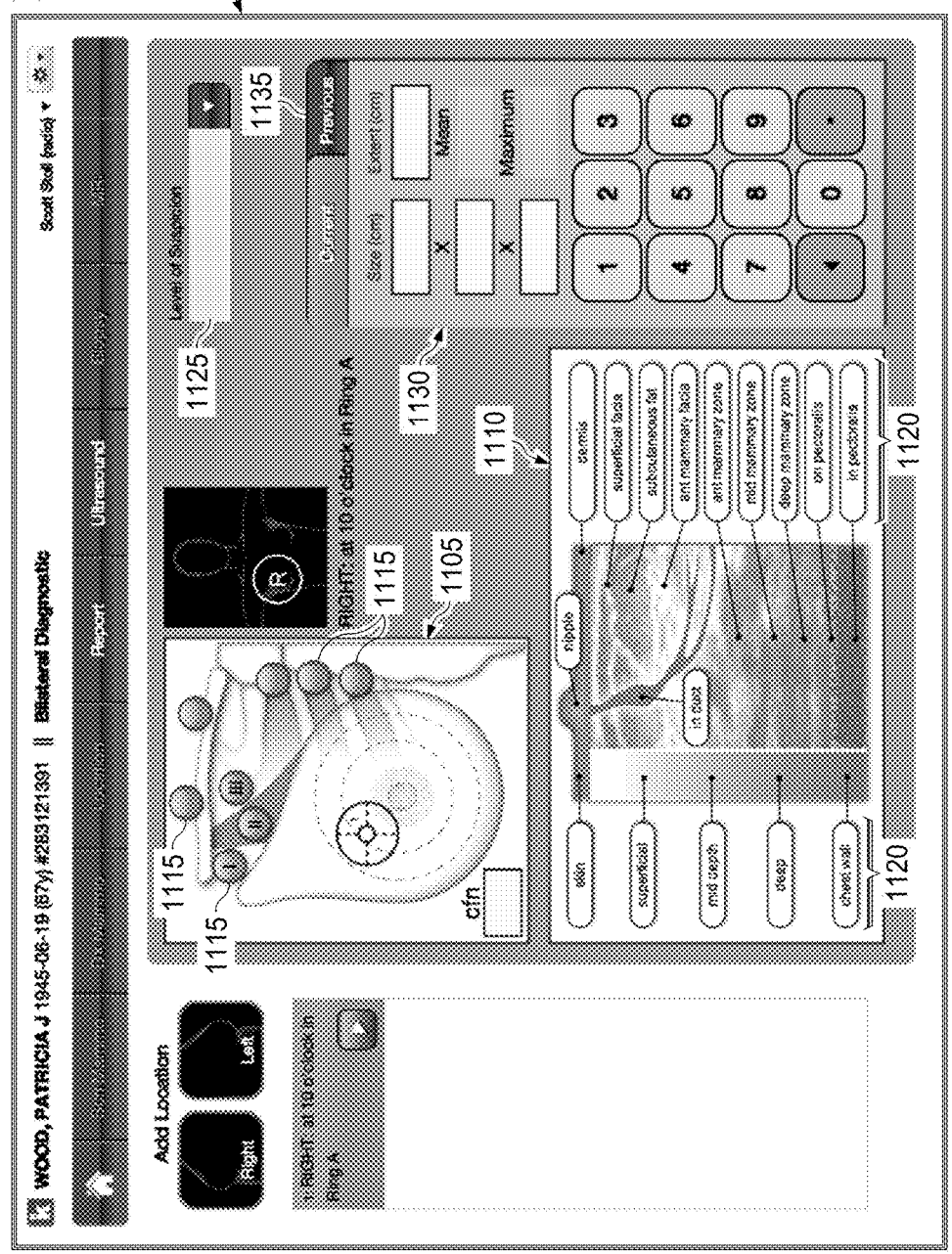
FIG. 11 illustrates an implementation of an example ultrasound graphical user interface.

In some implementations, the IMD system may generate GUIs corresponding to specific test results. For example, the IMD system may generate a GUI associated with ultrasounds, biopsy, and/or MRIs. FIG. 11 illustrates an implementation of an example ultrasound GUI 1100. As illustrated, the ultrasound GUI 1100 may allow an anatomical location to be provided and/or selected by a user. The ultrasound GUI 1100 may include one or more images that correspond to an anatomical location in patient test results. The images of anatomical locations in the ultrasound GUI may be representations of the anatomical image, rather than a photographic image and/or image from the patient test results. Since ultrasound scanning produces transverse views of an anatomical location, the ultrasound GUI 1100 may include a transverse view image (e.g., a schematic representation of a transverse view of an anatomical location). For example, the ultrasound GUI 1100 may include breast images, such as a first breast image (e.g., drawing) 1105 that includes representations of lymph nodes 1110 (e.g., proximate to the breast). As illustrated in FIG. 11, the first breast image 1105 may include level I, II, and/or III lymph nodes, other lymph nodes, the pectoral minor muscles and/or portions thereof. The ultrasound GUI 1100 may include breast images, such as a second breast image 1115 that illustrates a transverse view of the breast. The transverse view of the breast in the second breast image 1115 may allow a user to select an anatomical location based on relative location (e.g., skin, superficial, mid depth, deep, and/or chest wall) and/or anatomical location (e.g., dermis, subcutaneous fat, on pectoralis, duct, and/or nipple). A transverse view in conjunction with interpretation of ultrasound test results may allow more accurate locations to be selected by the user (e.g., because the ultrasound scans present a transverse view of an anatomical location) and/or may assist others in more accurately determining the location specified by the user. For example, a doctor performing a biopsy based on the location provided by the user may be more accurate due to the depiction using the first breast image 1105 and/or second breast image 1110. In some implementations, errors due to a user translating a location viewed on an ultrasound to a top or lateral view may be reduced by allowing location selection on a transverse view rather than and/or in addition to a lateral view.

A user may position a location indicator 1020 on one or more of the images 1105, 1110 on the ultrasound GUI. For example, the location indicator may be provided on a lymph node 1115 and/or one or more layers 1120 (e.g., relative depth and/or discrete region, such as in a duct, in subcutaneous fat, etc.) illustrated on the images 1105, 1110. Including a transverse view of an anatomical location may allow greater accuracy to be provided by a user providing a location, allow increased speed in providing an anatomical location since the user may not have to translate locations provided by the image in an ultrasound image to a side and/or top view (e.g., as opposed to a transverse view). The ultrasound GUI 1100 may include portions to provide a level of suspicion 1125 (e.g., independent of and/or in conjunction with a BI-RAD category) and/or sizes 1130 of lesions, masses, etc. The ultrasound GUI 1100 may allow information to be presented regarding previous patient test results 1135 such as size, level of suspicion, location, etc. The IMD system may retrieve the previous results from the patient record and/or a memory coupled to the IMD system.

In some implementations, the ultrasound GUI may be utilized independently and/or in conjunction with other GUI(s) generated by the system. For example, based on user properties, the IMD system may determine the GUI(s) to generate for presentation to the user.

In some implementations, a request for access to an ultrasound GUI, such as ultrasound GUI 1100, may be received. For example, a user may log into the IMD system and the IMD system may generate the ultrasound GUI. The ultrasound GUI may include breast images, such as a first breast image that includes representations of at least a portion of the lymph nodes proximate a breast and/or a breast image that includes a transverse view of the breast. The ultrasound GUI may include breast images such as the second breast image that includes a transverse view of the breast. The breast images may include a plurality of icons, such as location icons to denote relative location and/or anatomical location, such as lymph nodes and/or muscles. A user may select one or more locations via the location icons (e.g., select a side, select an anatomical location, and/or select a relative location). In some implementations, the user may select a BI-RAD category and/or level of suspicion to be associated with the selected location(s). The user may select and/or otherwise provide a dimension (e.g., size) to be associated with a characteristic (e.g., mass and/or calcification) in the test results via the GUI.

The selections provided by the user through the GUIs generated by the IMD system, such as selected icons (e.g., image icon(s) and/or text icon(s) such as association icon(s)) and/or anatomical location(s)), may be utilized by the IMD system to generate a report. The selections may be received via one or more GUIs generated by the IMD system, such as the work-list GUI, diagnosis GUI, location GUI, ultrasound GUI, etc. The report may include a diagnosis and/or be based at least partially on other information (e.g., patient history, exam history, user notes, follow-up tests to be recommended).

Figure 12:
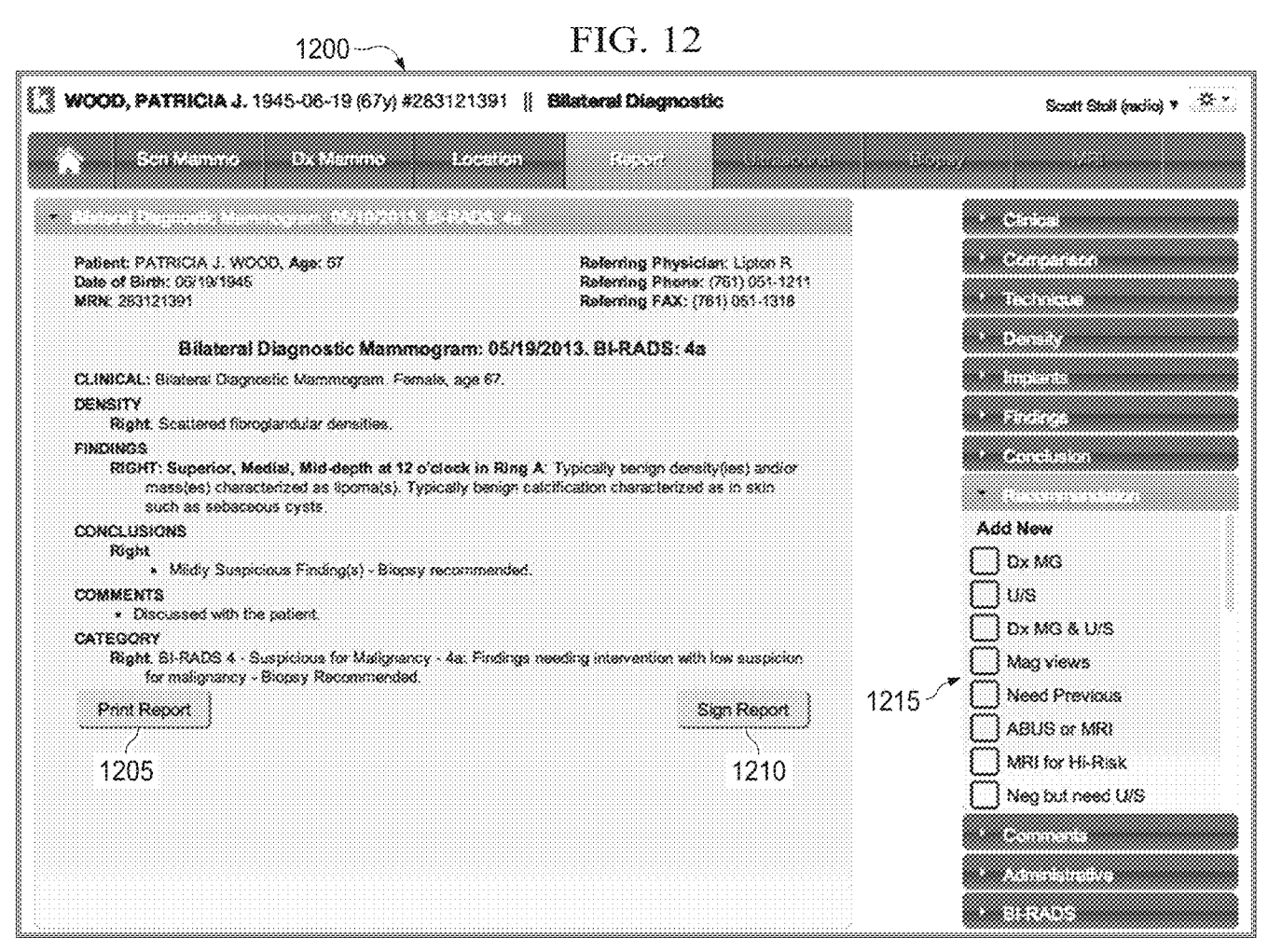

FIG. 12 illustrates an implementation of an example report GUI 1200. The report GUI 1200 may include diagnosis information such as a diagnosis. The IMD system may automatically generate the diagnosis information based on the selections provided by the user through the GUI(s), patient record(s), and/or government and/or industry standards. The report GUI 1200 may include may allow the diagnosis to be printed 1205 and/or signed 1210 by the user. For example, the report GUI may restrict transmission of the diagnostic report to, for example, an electronic medical record, a patient, and/or other physicians, prior to receiving approval (e.g., a signature) of a report by a user. The report GUI 1200 may allow additional information 1215 to be provided, for example, via one or more drop-down fields, tabs, etc. For example, the additional information 1215 may include information about additional testing, additional information needed to provide a diagnosis, comments, findings, etc.

The report may be generated concurrently with receiving the selections and/or when prompted by the user. For example, the user may select a report GUI tab and the report may be generated and/or presented to the user. In some implementations, a user may be inhibited from continuing to other portions of functionality of the IMD system without confirming (e.g., providing approval of) the diagnoses in the generated report. For example, the user may be restricted from enter diagnoses for other patients without confirming the diagnoses report generated by the IMD system. The user may be inhibited from logging out of the system until generated reports have been confirmed. In some implementations, a pop-up window, for example, may be presented to the user to remind the user that generated reports have or have not been confirmed. For example, the confirmation for generated reports reminder window may be presented to the user on a user device, such as the tablet displaying the GUI and/or via text message on a mobile phone. The confirmation for generated reports reminder window may be generated by the IMD system upon various triggers, such as user requesting access to GUI for a different patient, user requesting to log out, and/or passage of a predetermined period of time.

In some implementations, after the diagnostic report is confirmed by the user, the report and/or portions thereof may be automatically transmitted to one or more other parties (e.g., patients, physicians, other providers, and/or CDC or other agency). The IMD system may allow a user to create multiple reports that include different information from each other. For example, regulations (e.g., federal, community, state, and/or local) may govern what information is required to be transmitted to a patient. As another example, regulations may govern what information may not be transmitted (e.g., to the CDC such as patient identifying information). The IMD system may automatically include and/or restrict information in reports generated based at least in part on regulations. The IMD system may automatically include and/or restrict information in reports at least partially based on the identity of the person or entity that will receive the report. For example, reports may be generated including more detailed diagnosis information for referring physicians than reports generated for patients.

In some implementations, one or more of the generated GUIs may include default settings. Default settings may be based on user preferences and/or certain diagnoses, such as a negative result diagnosis. For example, a <no change> icon 125 may be automatically selected as a default setting and may indicate that no change has occurred since a previous diagnosis. The user may deselect (e.g., by touching or clicking) default settings, such as the <no change> icon, to change the default setting. In some implementations, default settings may be based at least partially on government and/or industry standards. For example, a user may be inhibited from signing a report when a breast density and/or BI-RADS® Category has not been provided.

Various portions of the IMD system and/or described processes may be utilized in conjunction with and/or independent of providing diagnoses of patient test results. For example, one or more features of the IMD system may be utilized to research characteristics, diagnoses, etc. The user may utilize the research in conjunction with analyzing a specific patient test result and/or independently. The IMD system may generate a GUI that includes image icons. A user may select an image icon and request one or more features of the IMD system. For example, a user may double-click or long-touch an image icon and a feature GUI, such as a pop-up window may be generated.

Figure 13:
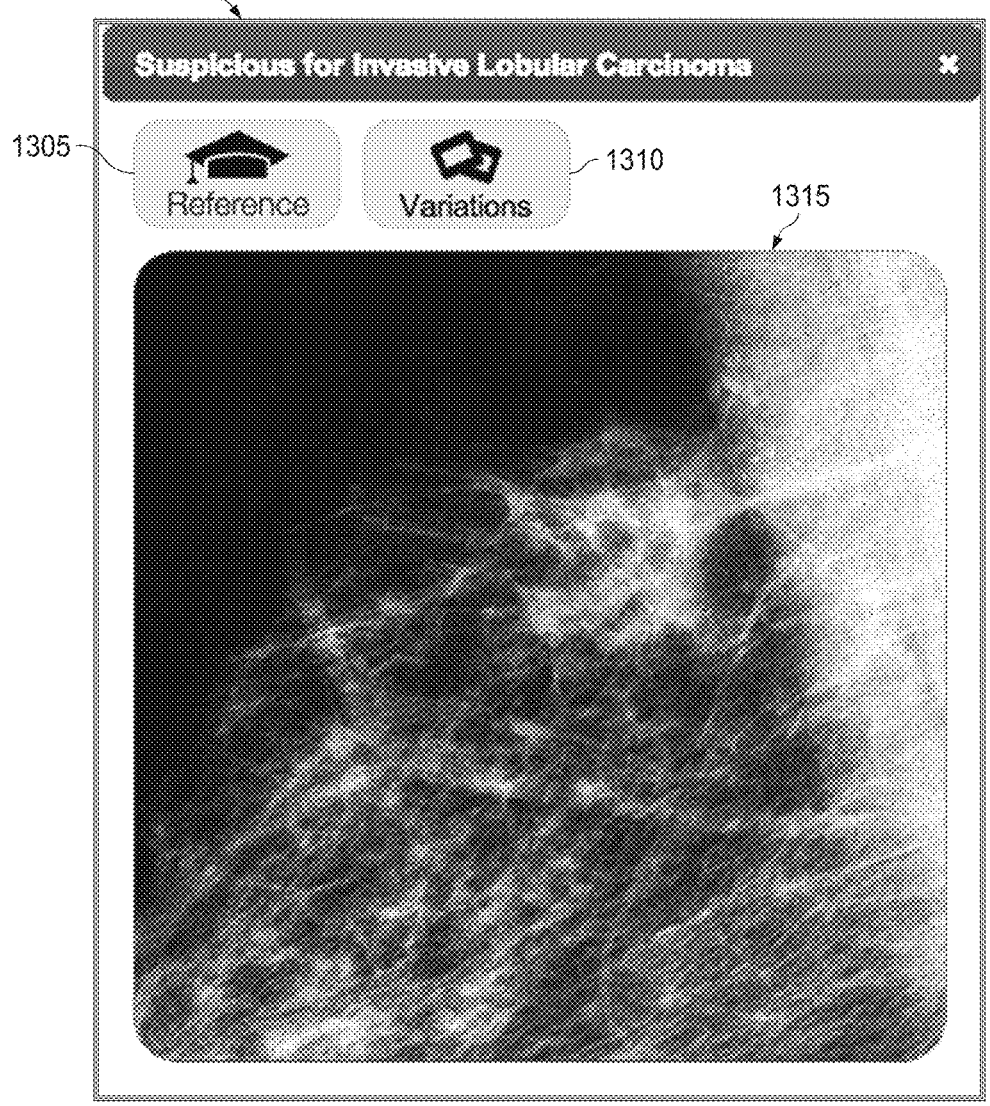
FIG. 13 illustrates an implementation of an example feature graphical user interface.

FIG. 13 illustrates an example of a feature GUI 1300. As illustrated, the feature GUI 1300 may include one or more icons through which features may be selected. For example, a user may request reference information related to the image icon using a <reference information> icon 1305 and/or variations in presentation of a characteristic in the image icon using a <variations> icon 1310. The feature GUI 1300 may include at least a portion of the photographic image in the selected image icon 1315.

In some implementations, the IMD system may allow a user to view variations in presentation of a characteristic included in an image icon. An expert, in some implementations, may select the image icons presented in a generated GUI. The GUI may initially display a selection of image icons based at least partially on user preferences, commonness of occurrence, type of medical image being analyzed, etc. A user may request more image icons (e.g., similar to a selected icon by selecting the <more other> icon and/or <more> image icons that include different presentations of similar diagnoses) through a feature GUI 1300. The IMD system may generate and/or display a different selection of image icons or other icons (e.g., one or more of the image icons may be different than the previously presented collection of image icons) based at least in part on the user request and/or parameters indicated in the user request. The user may or may not then select an image icon from the new selection of icons. The user may select among the image icons to select an image icon that may more accurately reflect a diagnosis or occurrence related to a diagnosis.

Figure 14:
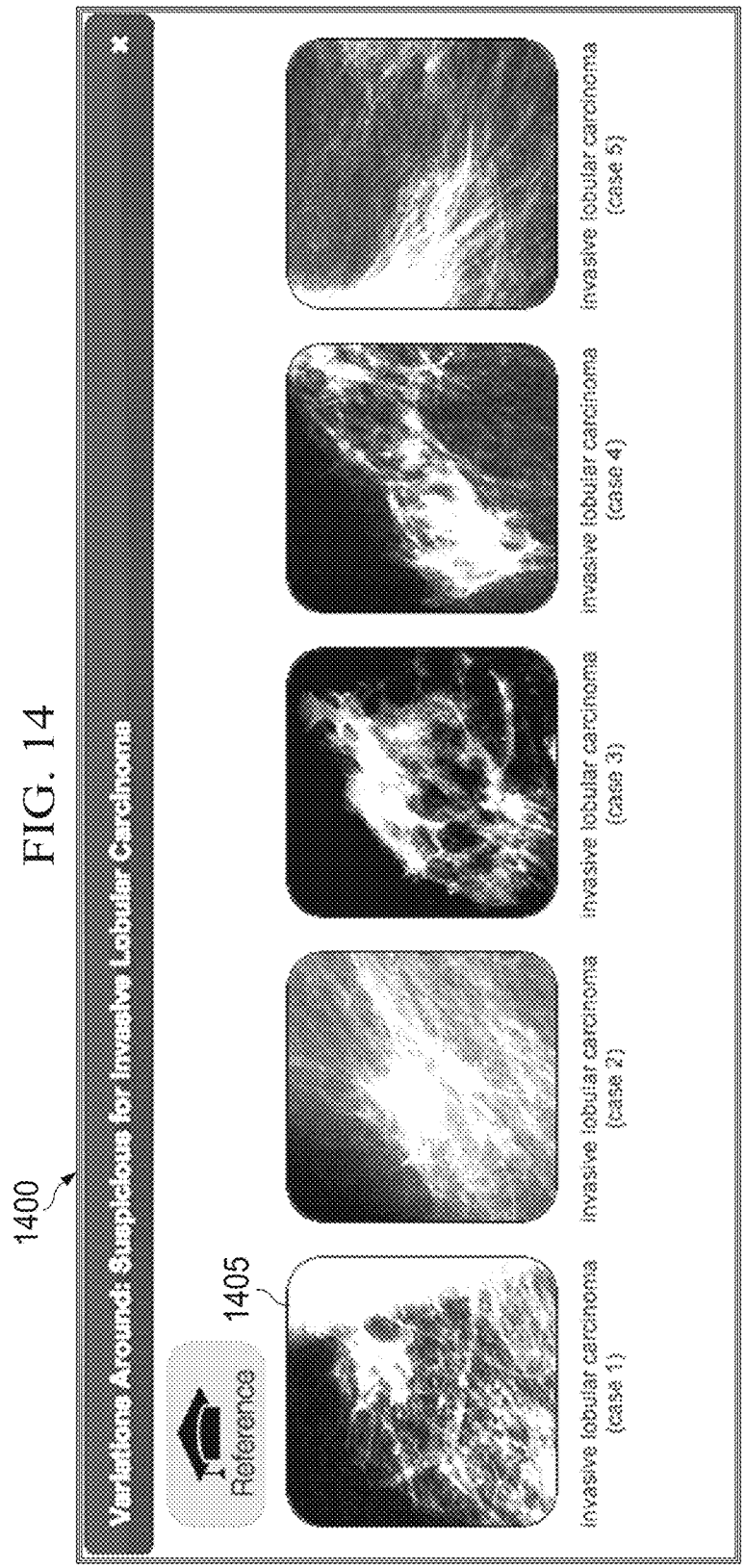
FIG. 14 illustrates an implementation of an example graphical user interface that presents variations of an image icon.

FIG. 14 illustrates an implementation of an example of GUI 1400 generated by the IMD system. The GUI 1400 includes variations 1405 in presentation of a characteristic in a selected image icon. For example, if a user selects a <variation> icon 1310 in the feature GUI 1300, then variations 1305 of the selected image icon may be presented through GUI 1400. The variations 1405 presented may be photographic images of different and/or similar presentations of a medical characteristic illustrated in a selected image.

In some implementations, a user may select (e.g., by double-clicking and/or selecting the image icon and an additional icon, such as a reference icon 1305 in features GUI 1305) an image icon to obtain reference information about diagnoses and/or occurrences related to the image icon. FIG. 1500 illustrates an example of a presentation 1500 of a reference material. As illustrated, a video related to an image icon is presented through a GUI generated by the IMD system. For example, during use, a user may be unsure of which image icon to select based on an analysis of a medical image of a patient. The user may select an image icon that appears similar to or approximately related to what the user views on a patient medical image, such as a PET scan. The user may select to view more image icons related to the selected image icon and/or to view reference material related to the image icon. In some implementations, a user may request reference material independently of the analysis of patient test results and/or patient records.

The GUI may retrieve and/or present reference material related to the image icon when requested by the user. The reference material may be correlated based on images and/or an indexed collection of a plurality of documents (e.g., expert opinions, journal articles, textbooks, etc.). By allowing the user to further research diagnoses related to the image icon using the GUI, the user's productivity may be increased and/or fatigue reduced due to decreased switching between right-brain and left-brain activity (e.g., because the user does not have to formulate key terms to search for information in a reference). The reference material collection may be searchable through key words and/or key word indexed, in some implementations. The collection of reference material may be updated at a central repository and users may access the updated information while utilizing the IMD system. Thus, the user may be able to access current information without lag times such as those commonly associated with receiving updates to reference textbooks and/or publications of new journal articles.

In some implementations, allowing the user to further research diagnoses related to an image icon may allow a user to research and/or diagnose an occurrence without knowing the appropriate key terms. For example, a user may see an occurrence in a medical image of a patient but not know what it is called or named. The user may select an image icon in the GUI that appears to be similar to the occurrence in the patient medical image. The user may then request more information about diagnoses related to the selected image icon and the GUI may retrieve and/or present reference material related to the selected image icon. The user may then confirm or deny suspicion about an occurrence and the diagnosis of the occurrence based on the presented research. Thus, a user may be able to more accurately provide diagnoses even without knowledge of the terms normally necessary to perform keyword-based search of references.

Although the IMA system, IMD system, diagnostic GUI(s) and/or analytical GUI(s) has been generally described in a medical environment (e.g., with medical images and/or medical diagnoses), the systems and processes described herein may be utilized with other expert images (e.g., test results) and diagnoses/analyses of the expert images. Expert images, such as test results, may include for example, CT scans, PET scans, MRI, radiographs, ultrasound, EEGs, EKGs, seismometers, seismic imaging systems, NMR, x-ray diffraction, GC, HPLC, skin lesions, dermatology findings, endoscopy findings, ophthalmology findings, pathological specimens including microscopic images, photographs, forensic images, and/or any other appropriate images. The system (e.g., IMA system and/or IMD system) and/or processes may generate a GUI to facilitate entry of diagnostic/analyses of the expert images and/or generate reports based on the diagnoses/analyses (e.g., for clients, for government agencies, and/or for billing).

For example, the system and/or processes may be utilized with expert images related to seismology and/or geology. Expert images presented to a user may include seismometer results and the user may provide analysis information through a GUI generated by the systems and/or processes described. The GUI may include image icons that correlate to typical patterns in a seismic image. For example, the image icons may be portions of a seismic image. The user may select an image icon to provide an analysis of a seismic image that the user is analyzing. If a user needs additional information (e.g., to facilitate analysis of the seismic image), the user may request more information about an image icon (e.g., by selecting an image icon and another icon or by double clicking an image icon). The system may retrieve and/or present to the user additional information such as seismology related expert opinions, reference materials, journal articles, etc. The system may generate a GUI to present the additional information to the user. The user may then utilize the system to select image icon(s) as an analysis of an expert image. The system may generate one or more reports (e.g., analysis reports, reports to government agencies, and/or billing reports) based on the selected image icon(s) and/or the corresponding analysis. The system may collect data based on the analysis entered by the user (e.g., performance statistics and/or reporting requirements for licensing). Probabilities of an outcome (e.g. presence or absence of petroleum within a geological location) may also be calculated and presented in the GUI utilizing system(s), process(es), and/or portions thereof similar to the described IMD system(s) and process(es) related to determining the probability of an outcome, such as malignancy in a medical environment.

As another example, the system and/or processes may be utilized with expert images related to structural analysis. Expert images may include x-ray and/or ultrasound images of structures and/or portions thereof (e.g., rebar positions, pier locations, column positions, and/or tendons in prestressed concrete). The expert images may be presented to a user. The system may generate a GUI that includes image icons and/or other icons for presentation to a user. The GUI may facilitate entry of an analysis of the expert images presented to the users. The system may communicate with other commercially available software (e.g., software for displaying images, analysis software, and/or computer aided design software). The system may transmit and/or retrieve information from the commercially available software and the information and/or portions thereof may be presented to the user through the GUI. For example, the system may determine communicate with commercially available image viewing software to ensure that the GUI generated is correlated to the appropriate case (e.g., the same case as associate with the expert image being viewed). The user may select image icon(s) and/or other icons that correspond to an analysis of the expert image(s) that the user is viewing. The user may also request more information about the image icon(s) and the system may retrieve reference material related to the image icon(s) selected. The reference material may assist the user in analyzing the expert images being analyzed by the user, in some implementations. Report(s) may be generated based on selected image icon(s) and/or other icon(s).

As another example, the systems and/or processes may be utilized with chemical analysis. The expert images may include results associated with gas chromatography, mass spectrometry, liquid chromatography, nuclear magnetic resonance, infrared analysis, and/or other appropriate images. The user may request access to a GUI of the system. The system may generate a GUI appropriate for the expert image being analyzed by the user. The GUI may include image icon(s) and/or other icon(s). The user may select image icon(s) and/or other icon(s) for selection in providing an analysis and/or to request additional information. Additional information, such as reference material (e.g., journal articles and/or expert images), may be presented to the user and/or may assist the user in selecting an appropriate analysis (e.g., and corresponding image icon(s)) for an expert image. Report(s) (e.g., to clients, to government agencies, and/or billing) may be generated based on the selection of image icon(s) and/or other icon(s). Various data may be tracked and/or stored by the system (e.g., dates analysis was performed, dates compounds were identified, user statistics, and/or billing statistics).

In some implementations, the various system(s) and/or processes may be utilized in forensic sciences. For example, a user may view expert images that include test results and provide analysis information through various GUIs. The system may generate reports, as appropriate.

In some implementations, various systems and/or processes may be utilized in astronomy. The expert images may include images (e.g., visible light based, electromagnetic radiation based, and/or neutrino based) of celestial bodies, for example. A user, such as an astronomer may view an expert image of an unknown area and analyze the expert image. The user may utilize GUIs generated by the system to enter in the analysis. The user may utilize the image icons to facilitate entry of the analysis into the GUI and/or to assist in the analysis of the GUI. For example, if the user does not know the appropriate analysis or image icon to select, the user may request more information about a similar image icon and the system may retrieve and/or present the additional information (e.g., reference materials) to the user.

Although several environments in which the IMA system and/or processes may be utilized have been described, the IMA systems and/or processes may be utilized in other environments, as appropriate.

In various implementations, the IMA system may include a computer system coupled to user device(s), one or more repositories, and/or third party system(s) via a network, such as the Internet. A user may view expert images, such as test results, via a third party system, on a user device. The user may provide an analysis of the presented test results via GUI(s) generated by the IMA system. For example, the IMA system may include one or more modules, stored on a memory of the IMA system and executable by a processor of the IMA system. The modules of the IMA system may validate user credentials, provide access to the IMA system, generate analytical graphical user interfaces, receive selections from a user via GUI(s), generate report(s) based on selection(s), monitor information (e.g., user information, metrics, and/or other information), etc. The IMA system may include an article that includes a machine-readable medium that stores instructions for generating analytical reports. The instructions may be operable to cause data processing apparatus to perform operations comprising one or more of the described operations.

In various implementations, the IMA system may generate an analytical graphical user interface comprising a plurality of image icons. A selection of image icon(s) may be received and a report may be automatically generated based on the selected image icon(s).

Implementations may include one or more of the following features. User information may be received (e.g., user credentials). The IMA system may determine whether to allow access to at least portions of the IMA system based at least partially on the provided user information. A record may be selected (e.g., a record associated with a test results). For example, the IMA system may generated a work-list (e.g., via a GUI) that includes records associated with test results to be analyzed. A user may select a record from the listing of records in the work-list. A request for test results to be presented on a user device via a third party system (e.g., commercially available software for viewing expert images) may be transmitted. In some implementations, the IMA system may determine whether a selected record is associated with test results presented to the user via third party software (e.g., by communicating via one or more application interfaces with at least a portion of the third party software). One or more analytical GUI(s) may be generated. For example, abbreviated analytical GUI(s), analytical GUI(s) related to a type of test result (e.g., ultrasound and/or NMR), and/or other types of analytical GUI(s) may be generated by the IMA system. In some implementations, the IMA system may allow and/or restrict selection of icons presented on the GUI (e.g., selection of predetermined types of icons may be restricted prior to receiving input, such as a location or other information). One or more of the generated GUIs may include image icons. The image icons may include a photographic image, such as a photographic image of an example of a characteristic (e.g., a characteristic of a result of an analysis, information related to a conclusion in an analysis, and/or other information related to an analysis). In some implementations, reports generated by the IMA system may include analytical reports, billing reports, metric reports, compliance reports, etc. The reports may be generated based on selections received through the GUI(s) generated by the IMA system and/or other information. In some implementations, one or more indicia (e.g., for image icons and/or locations) may be provided based on a previously generated report for the same record (e.g., patient, test subject, etc.). The IMA system may monitor properties of the user, store monitored properties, determine one of more metrics based on one or more monitored properties, and/or generate reports and/or notifications based on the metrics and/or monitored properties. The IMA system may receive follow-up information, such as outcomes (e.g., oil found at a location) and correlate the follow-up information to generated reports to determine metrics, such as probability of outcomes based on selection of one or more image icons. In some implementations, variations in presentation of a characteristic in an image icon may be requested by a user, retrieved, and/or presented to the user via GUI(s) generated by the IMA system.

In various implementations, the IMA system may include image-indexed references. The image-indexed references may be accessed independently and/or while providing analysis information through GUI(s) generated by the IMA system. For example, references may be correlated through one or more associations to image icons (e.g., in a similar manner as described in a medical environment). A request for reference information associated with at least one image icon of a GUI generated by the IMA system may be received, and reference information (e.g., a set of reference materials) may be retrieved from a memory, such as a database, coupled to the IMA system. The reference information may be indexed based on a first relation or association to an image icon. The reference information may be indexed based on a second relation to other references and/or other icons (e.g., similar presentations of characteristics and/or commonly confused analyses).

Although several operations performed by the IMA system have been described, other operations, such as described operations performed by the IMD system as appropriate in the environment in which the IMA is operating.

In various implementations, an analytical graphical user interface may be generated that includes a plurality of image icons. Each image icon may include a photographic image of an example of a characteristic. The analytical graphical user interface may generate one or more analyses related to one or more test results. A selection of image icon(s) related to analyzing test results may be received, and a report may be automatically generated that includes at least a portion of an analysis for test results based on at least one of the selected image icons.

Implementations may include one or more of the following features. The test results may include patient test results, and at least one of the analyses may include a diagnosis. One or more locations may be received via the generated graphical user interface, and a received anatomic location may identify at least a portion of a patient presented in at least one of the patient test results. The selected image icon(s) may be associated with at least one of the received locations. In some implementations, the test results may include patient test results, and at least one of the analyses may include a diagnosis. The image icon(s) may include a characteristic image icon that includes at least a portion of a photographic image associated with a medical characteristic. The image icon(s) may include breast density image icon(s) that include at least a portion of a photographic image associated with breast density. In some implementations, one or more indicia may be provided for one or more image icons based on a previously generated report for a record, where the test results are related to the record. The test results may include patient test results. In some implementations, at least one of the analyses may include a diagnosis, and one or more indicia may be generated based on a previously generated report for a patient. Each indicia may indicate an anatomic location in the patient, in some implementations. Properties of a user may be monitored and/or stored. Reports may be generated based on the monitored properties of the user. In some implementations, images of variations of the characteristic in the photographic image of an image icon may be retrieved based at least partially on the image icon selected. The image icons may include at least a portion of one or more CT scans, one or more mammograms, one or more radiographs, one or more MRI scans, one or more PET scans, one or more ultrasounds, and/or one or more other medical imaging exams. A number of image icons included on at least one of the generated graphical user interfaces may be automatically generated based at least partially on a screen dimension of a user device, where the graphical user interface is generated for presentation on the user device. At least one of the graphical user interfaces may include association icon(s), and at least one of the association icons may indicate a relationship between two or more selected image icons. Automatically generating a report may include retrieving one or more templates including words that include a diagnosis based on one or more of the selected image icons and one or more of the association icons. In some implementations, billing codes may be automatically generated based on at least one of the selected image icons or selected text icons of at least one of the graphical user interfaces.

In various implementations, one or more graphical user interfaces may be generated that include a plurality of image icons. Each image icon may include a photographic image of an example of a characteristic. At least one of the graphical user interfaces may facilitate generation of one or more analyses related to one or more test results. A selection of the image icon(s) related to analyzing test results, and a request for reference information associated with at least one of the selected image icons may be received. Reference information may be retrieved from a memory, such as a database. The reference information may be indexed based on relation to an image icon in the plurality of image icons.

Implementations may include one or more of the following features. A report that includes at least a portion of an analysis for test results ay be automatically generated based on at least one of the selected image icons. At least a portion of the retrieved reference information may be presented to a user. User properties may be monitored, and a listing of reference materials may be retrieved based at least partially on at least one of the monitored user properties.

In various implementations, an image based analytical system may include a report module and a memory. The report module may generate an analytical graphical user interface that includes a plurality of image icons, receive a selection of one or more of the image icons related to analyzing test results; and automatically generate a report that includes at least a portion of an analysis for test results based on at least one of the selected image icons. Each image icon may include a photographic image of an example of a characteristic, and the analytical graphical user interface may generate one or more analyses related to one or more test results. The memory may include template(s), and each template includes words that include at least a portion of an analysis based on one or more of the selected image icons.

Implementations may include one or more of the following features. The report module may determine one or more metrics. The report module may receive one or more follow up test results for a plurality of records, and may determine outcome(s) based on received image icon selections for the plurality of records and the received follow-up test results. The report module may communicate with a third party system such that test results are retrieved by the third party system.

In various implementations, a diagnostic graphical user interface may be generated that is related to patient test result(s) presented to a user via a third party interface. The graphical user interface may include image icon(s), and each image icon may include at least a portion of a medical photographic image of an example characteristic. Anatomical location(s) may be received via the generated graphical user interface, and a received anatomic location may identify at least a portion of a patient presented in at least one of the patient test results. A selection of the image icon(s) to associate with at least one of the received locations may be received. The image icons may be related to diagnosing patients. A report may be automatically generated that includes at least a portion of a diagnosis for a patient based at least partially on at least one of the selected image icons.

Implementations may include one or more of the following features. The diagnostic graphical user interface may include a breast imaging diagnostic graphical user interface, and the report may include at least a portion of the diagnosis of the patient based on breast imaging. The image icon(s) may include at least a portion of at least one of one or more CT scans, one or more mammograms, one or more radiographs, one or more MRI scans, one or more PET scans, one or more ultrasounds, and/or one or more other medical imaging exams. In some implementations, a selection of one or more image icons may be restricted when at least one anatomic location has not been received. A number of image icons included on the generated graphical user interface may be automatically adjusted based at least partially on a screen dimension of a user device, where the graphical user interface is generated for presentation on the user device. The graphical user interface may include text icon(s). A selection of an adjustment text icon may be received from a user, and the number of image icons included on the graphical user interface may be adjusted based on the received selection. One or more indicia may be generated based on a previously generated report for a patient. Each indicia may indicate at least one of an anatomic location in the patient and/or one or more image icons. In some implementations, one or more follow up test results may be received for a plurality of patients, and outcome(s) may be determined based at least partially on received image icon selections for the plurality of patients and the received follow-up test results. In some implementations, a selection of image icon(s) may be received for a new patient, and a probability of an outcome may be determined based on one or more of the received selections of image icons for the new patient and the previously determined outcomes. The graphical user interface may include association icon(s). At least one of the association icons may indicate a relationship between two or more selected image icons. Automatically generating a report may include retrieving template(s) that include words that include a diagnosis based on the selected image icon(s) and/or the association icon(s).

In various implementations, diagnostic graphical user interface(s) related to patient test results presented to a user via a third party interface may be generated. The graphical user interfaces may include image icon(s), and each image icon may include at least a portion of a medical photographic image of an example characteristic. At least one of the graphical user interfaces may include first diagnostic graphical user interfaces, and/or second diagnostic graphical user interfaces. The first diagnostic graphical user interfaces and/or the second diagnostic graphical user interface(s) may include anatomic location icon(s) and/or diagnostic text icons. Each anatomic location icon may indicate one or more locations on a patient. Each diagnostic icon may be associated with at least a portion of a diagnosis. At least one of the image icons of the first diagnostic graphical user interface may include a breast density image icon, and each breast density image icon includes at least a portion of a photographic image associated with breast density. At least one of the image icons of the second graphical user interface(s) may include breast density image icon(s) (e.g., that includes at least a portion of a photographic image associated with breast density) and/or lesion characteristic image icon(s) that include at least a portion of a photographic image associated with a medical characteristic of a lesion. Anatomical locations may be received via the generated graphical user interface(s), and each anatomic location may indicate at least a portion of a patient presented in at least one of the patient test results. A selection of image icon(s) to associate with at least one of the received locations may be received that is related to a diagnosis based at least partially on the presented patient test results, and a report may be automatically generated that includes at least a portion of a diagnosis for a patient based on at least one of the selected image icons.

Implementations may include one or more of the following features. A request from a user for a diagnostic graphical user interface may be received, and the first graphical diagnosis graphical user and/or the second diagnostic graphical user interface may be generated based at least partially on the request. A third diagnostic graphical user interfaces may include breast images, such as a first breast image that includes a representation of lymph nodes proximate a breast and/or a second breast image that includes a transverse view of a breast. A selection of a anatomic location on at least one of the breast images may be received, and the generated report may be based at least partially on the selection(s) in the third diagnostic graphical user interfaces. A determination may be made whether one or more locations have been received, and selections in one or more of the graphical user interfaces may be restricted if a determination is made that one or more locations have not been received. Billing codes may be automatically generated based on the image icon(s) selected and/or text icon(s) selected. Follow up information for a patient may be received and compared with the image icons previously selected for the patient. Metric(s) of a user may be determined based on the comparison, and at least one of the determined metrics of the user may be monitored.

In various implementations, an image based medical diagnostic system may include a report module and a memory. The report module may generate a graphical user interface related to patient test results that is presented to a user via a third party interface. The graphical user interface may include image icons, and each image icon may include at least a portion of a medical photographic image of an example characteristic. The report module may receive anatomical locations via the generated graphical user interface, and an anatomic location may indicate at least a portion of a patient presented in at least one of the patient test results. The report module may receive a selection of image icon(s) to associate with at least one of the received locations related to a diagnosis based at least partially on the presented patient test results, and may automatically generate a report that includes at least a portion of a diagnosis for a patient based at least partially on the selected image icon(s) and/or the template(s). A memory may include one or more templates, and each template may include words that include at least a portion of a diagnosis based on one or more of the selected image icons.

Implementations may include one or more of the following features. The report module may communicate with a third party system such that a patient test results are retrieved by the third party system. The image based medical diagnostic system may include a reference module that retrieves reference(s) based at least partially on an image icon selected. The reference module may retrieve image(s) of variations based at least partially on a image icon selected.

In various implementations, a graphical user interface, for presentation on a user device, may be generated. The graphical user interface may include a plurality of image icons, and each image icon may include at least a portion of a medical photographic image of an example characteristic. A selection of one or more of the image icons and a request for reference information associated with at least one of the selected image icons may be received. A first set of reference information may be retrieved from a memory, such as a database, based at least partially on at least one of the selected image icons. The reference information in the memory may be indexed based at least partially on one or more relationships to one or more of the image icons.

Implementations may include one or more of the following features. At least a portion of the retrieved reference information may be presented on the user device. In some implementations, a second set of reference information may be retrieved based on a secondary association. The secondary association may relate reference(s) in the second set of reference information with the first set of reference information and/or one of the selected image icons. At least a portion of the second set of reference information may be presented to a user. At least one of the image icons may include: characteristic image icon(s) that includes at least a portion of a photographic image associated with a medical characteristic; and/or breast density image icon(s) that include at least a portion of a photographic image associated with breast density. The generated graphical user interface may include association icons. A selection of association icon(s) may be received, and the first set of information may be retrieved based at least partially on the selected image icons and at least one of the selected association icons. The graphical user interface generated may be related to patient test result(s) presented to a user via a third party interface. In some implementations, anatomical location(s) may be received via the generated graphical user interface, where a anatomic location indicates at least a portion of a patient presented in at least one of the patient test results; a selection of image icon(s) to associate with at least one of the received anatomical locations may be received related to a diagnosis based at least partially on the presented patient test results; and, a report may be automatically generated that includes at least a portion of a diagnosis for a patient based on at least one of the selected image icons. Follow-up information may be received for one or more patients and compared with image icon(s) previously selected for each of the patients.

Errors based on a comparison of the follow up information and the image icons previously selected may be determined, and a third set of reference information may be identified based at least partially on the determined errors and/or the previously selected image icons associated with the determined errors. In some implementations, an error notification to a user based on the determined errors, wherein the error notification comprises a listing of the identified third set of reference information.

In various implementations, a graphical user interface may be generated that includes a plurality of image icons for presentation to a user. Each image icon may include at least a portion of a medical photographic image of an example of a characteristic. A selection of image icon(s) and a request for reference information associated with at least one of the selected image icon(s) may be received. A first set of reference information may be retrieved from a memory, such as a database, based at least partially on the selected image icons. Reference information in the database may be indexed based on relation to an image icon in the plurality of image icons.

Implementations may include one or more of the following features. At least a portion of the retrieved reference information may be presented on the user device. Image icons may include: a characteristic image icon that includes at least a portion of a photographic image associated with a medical characteristic; and/or a breast density image icon that includes at least a portion of a photographic image associated with breast density. The graphical user interface may include a plurality of other icons related to one or more diagnoses. A selection of one or more other icons and a request for reference information associated with at least one of the selected other icons may be received. A second set of reference information may be retrieved from a memory, such as a database, based on at least one of the selected other icons. The reference information in the database may be indexed based on relation to an other icon. The generated graphical user interface may include: breast images and/or other icons associated with breast images. The breast images may include a first breast image that includes a representation of a breast and lymph nodes proximate the breast, and a second breast image that includes a transverse view of the breast. A selection of an anatomic location on at least one of the breast images and selection of one or more other icons may be utilized to generate a diagnosis. In some implementations, a selection of at least one other icon and a request for reference information associated with at least one of the selected other icons may be received; and a second set of reference information may be retrieved from a memory, such as a database, based on at least one of the selected other icons. Reference information in the database may be indexed based on relation to an other icon. In some implementations, a listing of the first set of references may be generated and presented to a user. A selection of a reference from the listing may be received, and the selected reference may be retrieved.

In various implementations, an image indexed reference system may include a memory and an image-indexing module. The memory may store reference information and association(s) between reference information and image icon(s) in a graphical user interface that includes a plurality of image icons for presentation to a user. Each image icon may include at least a portion of a medical photographic image of an example of a medical characteristic. The image-indexing module may receive a selection of image icon(s) from the graphical user interface and a request for reference information associated with at least one of the image icons. The image-indexing module may determine a first set of reference information associated with the selected image icon based on at least one of the stored associations, and retrieve at least a portion of the first set of reference information from the memory.

Implementations may include one or more of the following features. The memory may store secondary associations between the reference information and the image icons. The image-indexing module may transmit a notification to the user based on the secondary association and the selected image icons, and retrieve at least a portion of a second set of reference information based at least partially on the secondary associations. The secondary associations may include related characteristics, similar characteristics, and/or misdiagnosed related characteristics. The image-indexing module may present at least a portion of the first set of reference information from the memory. The memory may store one or more variation images. The image-indexing module may receive a request for one or more variation images, and retrieve variation image(s) associated with at least one of the selected image icons. The information may include one or more expert verified references.

One or more of the described operations may be performed by data processing apparatus, where an article that includes a machine-readable medium stores instructions operable to cause the data processing apparatus to perform the described operations.

Although users have been described as a human, a user may be a person, a group of people, a person or persons interacting with one or more computers, and/or a computer system. Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

In various implementations, module(s) of the IMD system and/or IMA system, such as the diagnosis module may perform one or more of the operations as described in FIGS. 2-15.

One or more of the processes illustrated in FIGS. 2-15 or portions thereof may be implemented by various systems, such as the systems described in FIGS. 1A and/or 1B. In addition, various operations of FIGS. 2-15 or portions thereof may be added, deleted, and/or modified.

These computer programs (also known as programs, software, software applications or code) include machine instructions for a programmable processor, and can be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a track pad) by which the user can provide input to the computer. Other kinds of devices can be used to provide for interaction with a user as well; for example, feedback provided to the user by an output device can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other. Updates to the IMD system may be pushed to clients via a network.

It is to be understood the implementations are not limited to particular systems or processes described which might, of course, vary. As used in this specification, the singular forms "a", "an" and "the" include plural referents unless the content clearly indicates otherwise. Thus, for example, reference to "an image icon" includes a combination of two or more image icons and reference to "an icon" includes different types and/or combinations of icons. Although various operations have been described occurring "for each" user and/or patient, various implementations may include performing the operation for one or more users and/or patients, for one or more subset of users and/or patients, for more than one users and/or patients concurrently and/or sequentially.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular implementations of the process, machine, manufacture, composition of matter, means, methods and operations described in the specification. As one of ordinary skill in the art will readily appreciate from the disclosure, processes, machines, manufacture, compositions of matter, means, methods, or operations, presently existing or later to be developed that perform substantially the same function or achieve substantially the same result as the corresponding implementations described herein may be utilized according to the present disclosure. Accordingly, the appended claims are intended to include within their scope such processes, machines, manufacture, compositions of matter, means, methods, or operations.

The invention claimed is:

1. A method comprising:
    generating a graphical user interface to be presented on a user device, wherein the graphical user interface is related to one or more patient test results presented to a user via a third party interface, and wherein the graphical user interface comprises a plurality of image icons, and wherein each image icon comprises at least a portion of a medical photographic image of an example characteristic, and wherein the example characteristic is not a portion of the one or more patient test results presented via the third party interface;
    receiving a selection of one or more of the image icons of the graphical user interface;
    receiving a request for reference information associated with at least one of the selected one or more of the image icons; and
    in response to receiving the selection of one or more of the image icons and a request for reference information, retrieving a first set of reference information, based on one or more of the selection image icons, from a second set of reference information stored in a database; wherein the first set of reference information is based on more than one selected image icon when more than one of the image icons are selected; and wherein the second set of reference information does not include patient medical history associated with the one or more patient test results presented via the third party interface; and wherein the second set of reference information stored in the database is indexed based at least partially on one or more relationships to one or more of the image icons in the plurality of image icons of the graphical user interface;
    receiving one or more follow up test results for a plurality of patients; and
    determining one or more outcomes based on received image icon selections for the plurality of patients and the received follow-up test results;
    determining a probability of an outcome based on one or more of the selected image icons for the patient and one or more of the previously determined outcomes.

2. The method of claim 1 further comprising presenting at least a portion of the retrieved first set of reference information on the user device.

3. The method of claim 1 further comprising:
    determining a third set of reference information based on a secondary association, wherein the secondary association relates one or more references in the third set of reference information with one of the selected image icons; and
    presenting at least a portion of the third set of reference information to the user.

4. The method of claim 1 wherein at least one of the image icons comprises at least one of:
    a characteristic image icon, wherein the characteristic image icon comprises at least a portion of a photographic image associated with a medical characteristic; or
    a breast density image icon, wherein the breast density image icon comprises at least a portion of a photographic image associated with breast density.

5. The method of claim 1 wherein the generated graphical user interface comprises association icons; and wherein receiving the selection of one or more of the image icons comprises receiving a selection of more than one image icon, and further comprising:

receiving a selection of one or more of the association icons;

wherein the first set of reference information is retrieved based on more than one of the selected image icons and at least one of the selected association icons.

6. The method of claim 1 further comprising:

receiving one or more anatomical locations via the generated graphical user interface, wherein the one or more anatomic locations indicates at least a part of the portion of the patient presented in the one or more patient test results;

receiving a second selection of one or more of the image icons to associate with at least one of the received anatomical locations, and wherein the second selection is related to a diagnosis based at least partially on one or more of the presented patient test results; and automatically generating a report comprising at least a portion of the diagnosis for the patient based on at least one of the second selection of one or more of the image icons.

7. The method of claim 6 further comprising:

receiving follow up information for one or more patients;

comparing follow up information with one or more of the image icons previously selected for each of the one or more patients;

determining errors based on a comparison of the received follow up information and one or more of the image icons previously selected for each of the one or more patients; and identifying a third set of reference information based at least partially on the determined errors and one or more of the previously selected image icons associated with the determined errors.

8. The method of claim 7 further comprising: transmitting an error notification to the user based on the determined errors, wherein the error notification comprises a listing of the identified third set of reference information.

9. The method of claim 1 further comprising:

transmitting a notification to the user based on at least one secondary association and one or more of the selected image icons, wherein at least one of the secondary associations designates an association between at least one reference of the first set of reference information and at least one of the selected image icons, and wherein at least one of the secondary associations comprises at least one of: related characteristics, similar characteristics, or misdiagnosed related characteristics;

retrieving a third set of reference information based at least partially on the at least one secondary association.

10. The method of claim 1 further comprising:

receiving a request for one or more variation images; and retrieving one or more of the variation images associated with at least one of the selected image icons.

11. The method of claim 1 wherein the reference information comprises one or more expert verified references.

12. The method of claim 1 wherein two or more image icons selections are received, and further comprising:

receiving a request for one or more variation images related to two or more of the selected image icons; and retrieving one or more of the variation images associated with the two or more of the selected image icons;

presenting one or more of the retrieved variation images;

receiving a selection of at least one of the two or more of the selected image icons; and generating a diagnosis report based at least partially on the received selection of at least one of the two or more of the selected icons.

13. The method of claim 1 wherein the graphical user interface further comprises:

a plurality of diagnostic icons; and one or more association icons;

wherein one or more of the image icons comprises one or more breast image icons, and wherein receiving the selection of one or more of the image icons comprises:

receiving a selection of at least one of the breast image icons;

receiving a selection of at least one of the associations icons; and receiving a selection of at least one of the diagnosis icons;

and wherein retrieving the first set of reference information comprises retrieving a first set of reference information based on the received selection of at least one of the breast image icons, the received selection of at least one of the association icons, and the received selection of at least one of the diagnosis icons.

14. The method of claim 1 wherein one or more of the image icons comprises one or more lesion characteristic icons, and wherein receiving the selection of one or more of the image icons comprises receiving a selection of at least one lesion characteristic icon, and wherein retrieving a first set of reference information is based at least partially on one or more of the selected lesion characteristic icons.

15. A method comprising:

generating a diagnostic graphical user interface to be presented on a user device, wherein the diagnostic graphical user interface is related to one or more patient test results, and wherein the one or more patient test results are presented to a user via a third party interface, and wherein the graphical user interface comprises one or more image icons, and wherein each image icon includes at least a portion of a medical photographic image of an example characteristic, and wherein the example characteristic is not a portion of the one or more patient test results presented via the third party interface, and wherein one or more of the image icons includes one or more breast image icons that include at least a portion of a characteristic of a portion of a breast in mammography;

receiving a selection, via the generated graphical user interface, of one or more anatomical locations, wherein each received anatomic location identifies a part of the patient presented in the one or more patient test results, and wherein at least one of the received anatomical locations is proximate the breast or in the breast;

receiving a selection of one or more of the image icons to associate with at least one of the previously received anatomical locations, wherein one or more of the selected image icons are related to diagnosing the patient; and automatically generating a report comprising at least a portion of a diagnosis for the patient based on at least one of the selected image icons and at least one of the associated previously received anatomical locations;

receiving one or more follow up test results for a plurality of patients; and determining one or more outcomes based on received image icon selections for the plurality of patients and the received follow-up test results;

determining a probability of an outcome based on one or more of the selected image icons for the patient and one or more of the previously determined outcomes.

16. The method of claim 15 wherein at least one of the image icons comprises a lymph node image icon, and wherein the lymph node image icon includes at least a portion of a characteristic of a lymph node located proximate a breast, and wherein at least one of the selected image icons comprises the lymph node image icon.

17. The method of claim 15 wherein one or more of the selected image icons comprises one or more breast image icons, and the further comprising:
   receiving a request for one or more variation images related to at least one of the selected breast image icons; and
   retrieving one or more of the variation images associated with a photographic image included in the at least one of the selected breast image icons.

18. The method of claim 15 further comprising:
   generating one or more second diagnostic graphical user interfaces comprising breast images, and wherein the breast images include:
      a first breast image comprising a representation of lymph nodes proximate a breast; and
      a second breast image comprising a transverse view of the breast; and
   receiving a second selection of a second anatomic location on at least one of the breast images; and
   wherein the generated report is based at least partially on one or more of the second selections in the one or more second diagnostic graphical user interfaces.

19. The method of claim 15 wherein one or more of the breast image icons comprises one or more breast density image icons, and wherein each of the breast density image icons comprises at least a portion of a photographic image associated with breast density.

20. The method of claim 15 further comprising automatically generating billing codes based on at least one of:
   one or more of the selected image icons
   or one or more text icons selected by the user.

21. The method of claim 15 wherein at least one of the image icons selected comprises at least one of the breast image icons, and further comprising:
   receiving a request for reference information associated with at least one of the selected breast image icons; and
   retrieving a first set of reference information from a database based on at least one of the selected image icons, wherein the reference information in the database is indexed based at least partially on one or more relationships to one or more of the image icons in the plurality of image icons.

22. The method of claim 15 wherein at least one of the breast image icons comprises a legion icon associated with the breast or an area proximate to the breast, and wherein the graphical user interface comprises one or more diagnostic icons, and wherein receiving a selection of one or more of the image icons comprises receiving a selection of at least one of the legion icons;
   and further comprising receiving a selection of one or more of the diagnostic icons, and wherein automatically generating the report comprises automatically generating the report based at least partially on one or more of the selected legion icons and one or more of the selected diagnostic icons.

* * * * *